(12) United States Patent
West

(10) Patent No.: US 11,382,830 B1
(45) Date of Patent: Jul. 12, 2022

(54) SEMICONDUCTOR ACUPUNCTURE DEVICE AND METHOD OF USE

(71) Applicant: Fred D. West, Austin, TX (US)

(72) Inventor: Fred D. West, Austin, TX (US)

( * ) Notice: Subject to any disclaimer, the term of this patent is extended or adjusted under 35 U.S.C. 154(b) by 0 days.

(21) Appl. No.: 17/230,811

(22) Filed: Apr. 14, 2021

(51) Int. Cl.
| | |
|---|---|
| *A61H 39/08* | (2006.01) |
| *A61H 39/00* | (2006.01) |
| *H01L 21/02* | (2006.01) |
| *C23C 14/08* | (2006.01) |
| *A61N 1/375* | (2006.01) |
| *A61N 1/36* | (2006.01) |
| *A61N 1/05* | (2006.01) |

(52) U.S. Cl.
CPC ......... *A61H 39/086* (2013.01); *A61H 39/002* (2013.01); *A61N 1/36017* (2013.01); *A61N 1/3756* (2013.01); *C23C 14/088* (2013.01); *H01L 21/02197* (2013.01); *H01L 21/02565* (2013.01); *A61H 2201/5007* (2013.01); *A61N 1/0502* (2013.01); *A61N 1/0504* (2013.01)

(58) Field of Classification Search
CPC ................ A61H 39/086; A61H 39/002; A61H 2201/5007; A61N 1/36017; A61N 1/3756; A61N 1/0502; A61N 1/0504; C23C 14/088; H01L 21/02197; H01L 21/02565
See application file for complete search history.

(56) References Cited

U.S. PATENT DOCUMENTS

| | | | |
|---|---|---|---|
| 3,861,392 A | 1/1975 | Moen | |
| 3,957,053 A | 5/1976 | Woo | |
| 5,250,068 A | 10/1993 | Ideguchi et al. | |
| 6,493,588 B1 | 12/2002 | Malaney et al. | |
| 8,855,737 B2 | 10/2014 | Clark et al. | |
| 9,480,836 B2 | 11/2016 | Na | |
| 9,801,559 B2 | 10/2017 | Jamieson et al. | |
| 10,213,363 B2 | 2/2019 | Ding et al. | |
| 2002/0183804 A1 | 12/2002 | Malaney et al. | |
| 2005/0070948 A1 | 3/2005 | Kirsteins | |
| 2013/0110150 A1 | 5/2013 | Yoo et al. | |
| 2015/0148643 A1 | 5/2015 | Small et al. | |
| 2015/0352007 A1 | 12/2015 | Shayle | |
| 2016/0073887 A1 | 3/2016 | Lee et al. | |

FOREIGN PATENT DOCUMENTS

JP 4020221877 A * 1/1990

OTHER PUBLICATIONS

Full machine translation of JP 4020221877A Jan. 24, 1990.*

* cited by examiner

*Primary Examiner* — Mark W. Bockelman
(74) *Attorney, Agent, or Firm* — Scheinberg & Associates, P.C.

(57) ABSTRACT

Semiconductor electroacupuncture needles are disclosed, as well methods of making and using the semiconductor electroacupuncture needles. A controller for controlling the characteristics of the voltage applied to the needles and/or the current flowing through the needles is described. In some embodiments, a portion of the electro acupuncture needle is insulated to control the position below the skin at which the current enters the patient. In some embodiments, an LED on the needle lights when current above a threshold value is passing through the needle and into the patient.

26 Claims, 21 Drawing Sheets

SEMICONDUCTOR ACUPUNCTURE DEVICE AND METHOD OF USE

FIELD OF THE INVENTION

This disclosure relates generally to electroacupuncture, in particular to electroacupunctures formed from a semiconductor material.

BACKGROUND OF THE INVENTION

Electroacupuncture is where a small electric current is passed between pairs of electroacupuncture needles. Current electroacupuncture needles are made of stainless steel, silver, and gold. These needles are available in various lengths from 0.5 inches (13 mm) to 5.0 inches (125 mm). Needle thickness range from 0.0047 inches (0.12 mm) to 0.0137 inches (0.35 mm). An electrode is provided for connecting to a power source. The power source for current electropuncture needles is a 9-volt, or similar voltage. Connection to the electroacupuncture needle is provided by a connecting wire and an alligator clip.

Current acupuncture needles are inserted into the body at specific points and depths identified by traditional Chinese medicine. These stainless needles have multiple surface imperfections resulting in discomfort when inserted, "Acupuncture in Medicine," 2014 April; 32 (2) 146-154: https://doi.org/10.1136/acupmed-2013-010472. Most electroacupuncture needles are made of stainless steel and do not support high electron flow or current flow. Current flow is reduced in stainless steel electroacupuncture due to the use of Chromium in the manufacturing process creating stainless steel.

Electroacupuncture involves the insertion of a multiple conventional acupuncture needles into the body and a varying voltage is supplied to each needle as anode and cathode. This creates a flow of electrons from the body of one acupuncture needle to another. The objective is for the flow of electrons at nerve junctions to be high enough to block signals coming from that junction to the brain.

Electron flow will always follow the path of least resistance. The resistance to the flow of electrons is less across the skin surface and more through the tissue of the body the acupuncture needle is inserted into. Therefore, with prior art electroacupuncture needles, most of the current flowing between the acupuncture needles goes across the surface of the skin, resulting in less current being available to block signals at the nerve junction that is being targeted. Minimal signal blockage of the pain receptors results in less pain relief for shorter periods of time. Therefore, the use of electroacupuncture to help relieve pain has been limited due to the materials being used for the needles themselves and prior art electroacupuncture depends largely on the placebo effect.

Electroacupuncture depends on the application of an electrical current and varying frequency to block pain signals. Electroacupuncture can provide a measure of pain relief for a limited time based on the depolarization of the nerve junction blocking the pain receptors if there is sufficient electrical current at the correct frequency.

FIG. 1 shows a front view of typical electroacupuncture needle 102 made of stainless steel, gold, silver, or some other homogenous material 106. The homogenous material 106 has numerous microscopic bumps and imperfections resulting in discomfort when inserting electroacupuncture needle. Acupuncture in Medicine. 2014 April; 32(2) 146-154 https://doi.org/10.1136/acupmed-2013-010472. An electrode 104 provides a connection point for a clip or alligator clip to provide power to the electroacupuncture needle 102. FIG. 2 shows a side view of such a needle that has a flattened or squared electrode 104, which facilitates the connection of a power source to the electroacupuncture needle.

Current flow is generated along the entire length of electroacupuncture needle 102. This current flow, when using a standard 9 Volt battery to provide power, is approximately 0.039984 coulombs for iron and 0.027989 coulombs for stainless steel. This significant difference between the current flow exhibited in iron versus Stainless steel is due to Stainless steel containing a minimum of 11% chromium. This incorporation of chromium results in a 30% to 40% reduction in current flow when comparing Stainless steel needles versus iron needles due to the disruption in the lattice structure of iron.

SUMMARY OF THE DISCLOSURE

An object of the invention is to provide a method and apparatus for improved electro acupuncture.

Electroacupuncture needles manufactured from semiconductor materials are disclosed. These electroacupuncture needles provide greater electron and current flow between two or more acupuncture needles inserted into humans or non-humans than those made of the current metallic materials.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION

Figure 1:
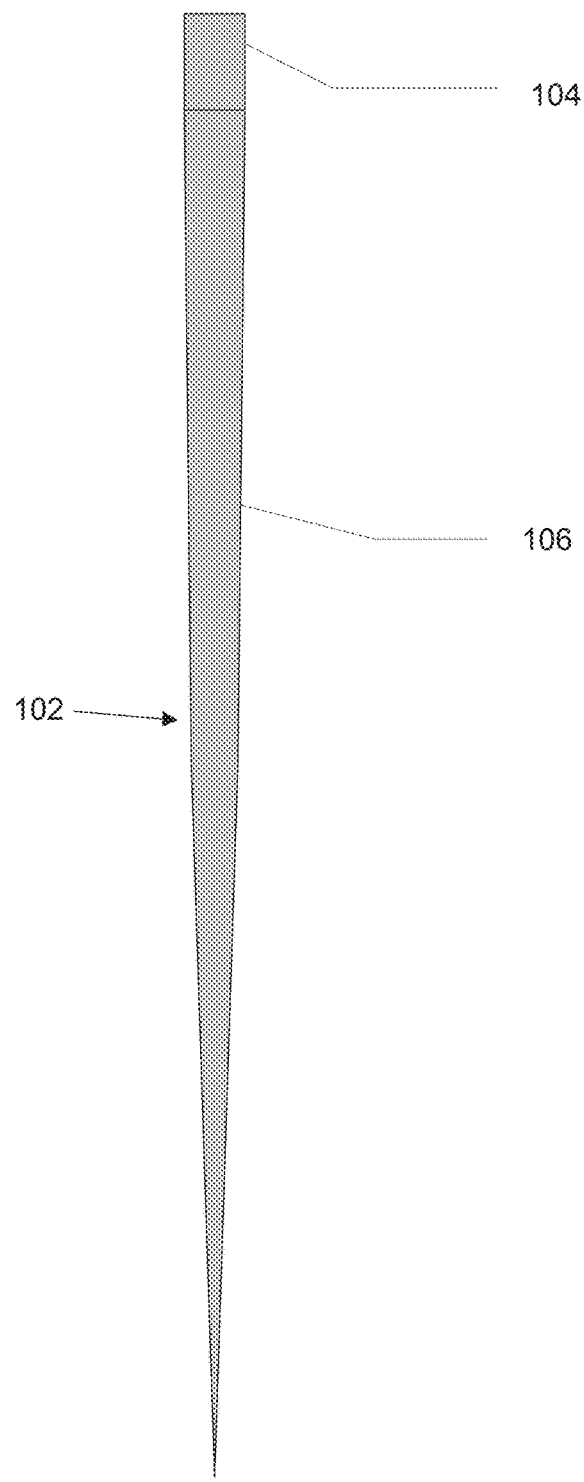
FIG. 1 is a front view of a prior art electroacupuncture needle made of stainless steel, gold, silver, or some other homogenous material.
Figure 2:
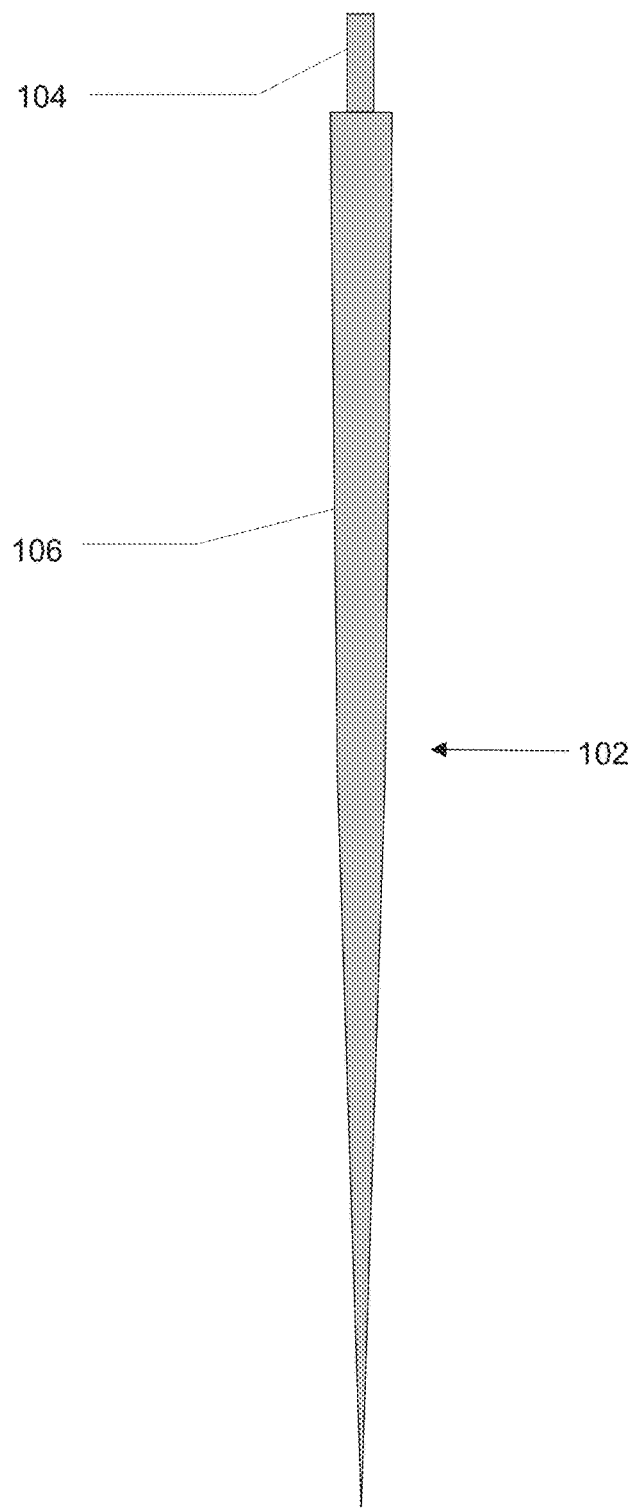
FIG. 2 is a side view of the electroacupuncture needle of FIG. 1.
Figure 3:
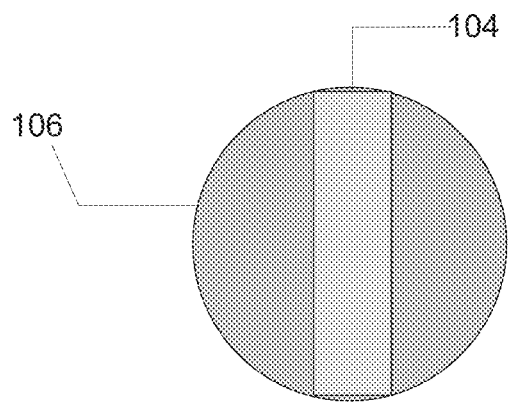
FIG. 3 is a top view of the electroacupuncture needle of FIG. 1 showing the tab for attaching an alligator clip for the application of electrical power to the electroacupuncture needle.

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized, and that logical, mechanical, electrical and other changes may be made without departing from the scope of the implementations. The following detailed description is, therefore, not to be taken in a limiting sense.

Semiconductor electroacupuncture needles provide greater electron and current flow between two or more acupuncture needles inserted into humans or non-humans that those made of the current metallic materials. This counterintuitive result is the consequence of current flow increasing linearly with voltage with iron and other traditional electroacupuncture needle materials but increasing exponentially in semi-conductors. Thus, while current flow may be higher in traditionally made electroacupuncture needles at lower voltage, ones made from semiconductors will exhibit higher current flow when voltages are sufficiently increased. The present invention involves semiconductor electro acupuncture needles, and processes to make and use semiconductor needles. Semiconductor electroacupuncture needles may be manufactured using a variety of materials. Because semiconductor electroacupuncture needles exhibit fewer surface imperfections than traditional electroacupuncture needles, the semiconductor electroacupuncture needles can be inserted into the skin with less tissue damage and discomfort than traditional electroacupuncture needles.

Electroacupuncture needles manufactured from primarily non-toxic semiconductor materials provide greater electron and current flow between two or more acupuncture needles inserted into humans or non-humans for the treatment of various medical conditions. A few of these various conditions are muscle relaxation, pain relief, some psychological conditions, drug addiction, stroke rehabilitation. The semiconductor electroacupuncture needles may be manufactured using a variety of semiconductor materials, some of the materials may be toxic. The toxic material added to the semiconductor electropuncture needle is for treatment of specific conditions known to respond to various toxic materials used in small dosages. Semiconductor electroacupuncture needles provide a significant increase in electrons present at nerve conduction points which transmit signals from a location in or on the human body to the brain using the human body's nervous system. The increased electron flow effectively depolarizes the nerve junction resulting in the blockage of the signal from the nerve junction to the brain. The increased electron flow may also have the effect of increasing the electrical or chemical (Reference: https://www.sciencedirect.com/science/article/pii/B978012512504850007X) signal through a nerve junction. This signal may be a pain receptor, discomfort, non-functional nerve junction (Such as results of a stroke for example), or a signal perceived as "abnormal" in some way. Semiconductor material acupuncture needles have fewer surface imperfections than stainless steel resulting in nearly painless insertion into human/non-human tissue.

Semiconductor electroacupuncture needles provide a significant increase in electrons present at nerve conduction points which transmit signals from a location in or on the human body to the brain using the human body's nervous system as compared to their traditional counterparts. The increased electron flow more effectively depolarizes the nerve junction resulting in the blockage of the signal from the nerve junction to the brain. The increased electron flow may also have the effect of increasing the signal through a nerve junction. This signal may be a pain receptor, discomfort, non-functional nerve junction (Such as results of a stroke for example), or a signal perceived as "abnormal" in some way. Semiconductors can be doped with other elements and materials, including those that are toxic. The semiconductor electroacupuncture needles are no different. Medical professionals frequently treat certain conditions using toxins at low doses and said compounds may be incorporated into the semiconductor electroacupuncture needles for use by medical professionals or those properly trained and certificated.

Figure 4:
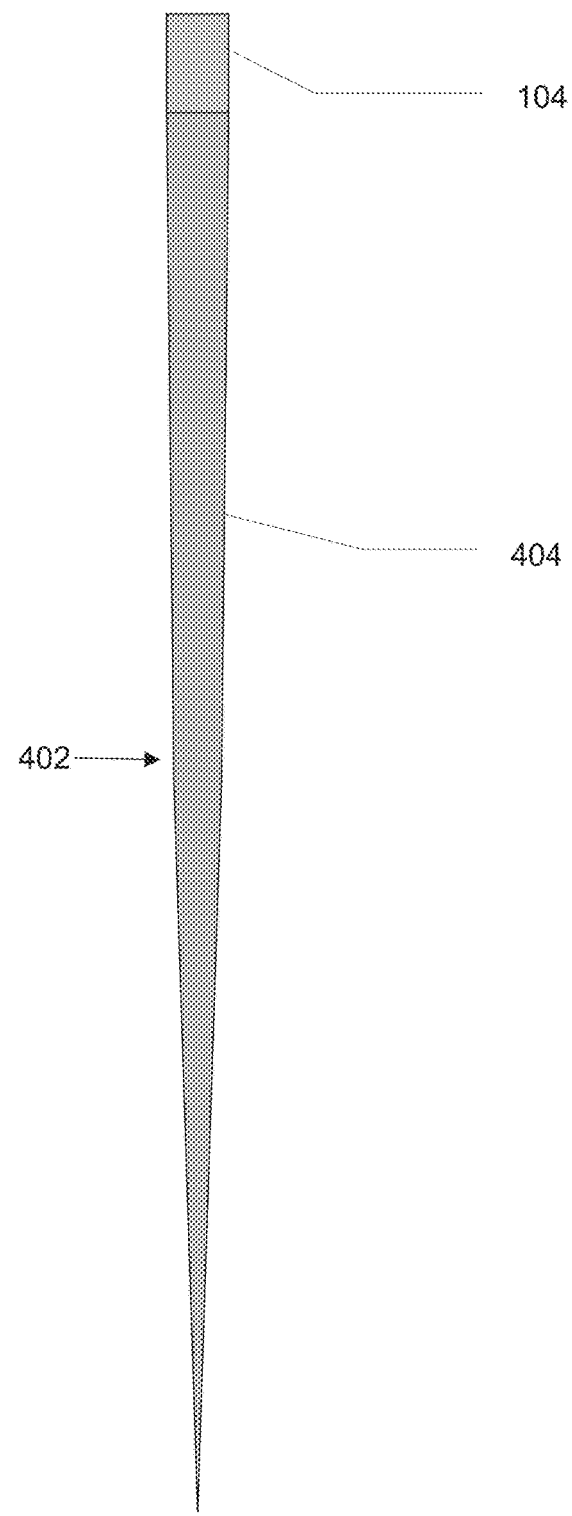
FIG. 4 is a front view of semiconductor electropuncture needle made of a variety of semiconductor materials to meet specific treatment requirements.
Figure 5:
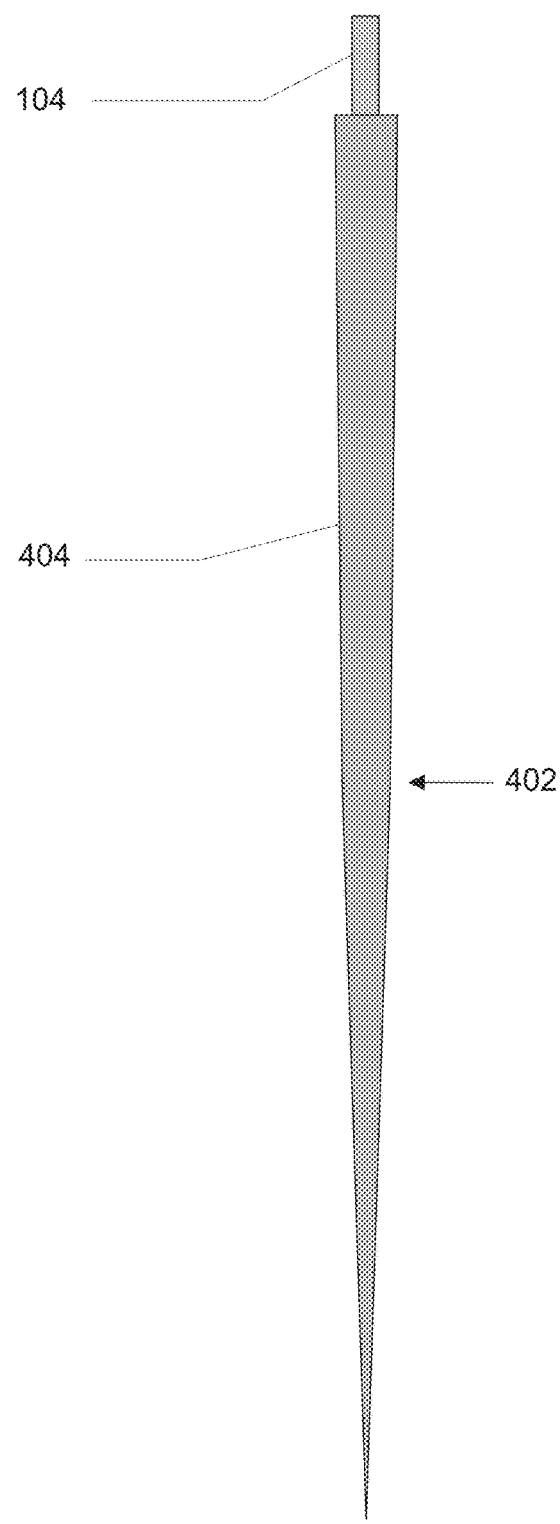
FIG. 5 is a side view of semiconductor electroacupuncture needle showing the electrode tab for connecting to electrical power.

FIG. 4 is a front view of a semiconductor electropuncture acupuncture needle 402 which may be made of a variety of semiconductor materials to meet specific treatment requirements. The primary embodiment contemplates the use of barium, titanium, and oxygen using the chemical formula of $BaTiO_3$ for the electroacupuncture needle 402. This combination has a beneficial quality in that it is a non-toxic semiconductor material combination.

A preferred embodiment contemplates the formula for the semiconductor's tertiary compound to be in the form of $Ba_xTi_{1-x}O_3$ with the typical value for "x" is 0.55. In other embodiments, other non-toxic semiconductor materials may be used such as bismuth, gallium aluminum, gallium nitride, sulfur, sodium bismuth, and platinum. Other semiconductor compounds from binary to quaternary compounds may be used to meet differing requirements. Cleaving the finished wafer is done by mounting the wafer on tape and using a mechanical dicing saw, dicing saw, and laser cutting. Semiconductor wafers when cut by laser have surface imperfections measured in nanometers. To compare with stainless steel, one can see: https://www.ncbi.nlm.nih.gov/pmc/articles/PMC3995252/. Electrical power and other inputs are inserted into the needle through the electrode 104 and current is generated along the entire length of semiconductor material.

The addition of very small amounts of biologically active materials, some of which may be toxic in large doses, to the semiconductor material 404 may provide enhanced treatment for various medical issues such as cancer, psychological treatments, muscle relaxation, stroke rehabilitation, and possibly other conditions. As an example, the toxic material arsenic is added to the semiconductor material 404 yielding the semiconductor material formula of $BaTiAsO_3$. Arsenic is known to be an effective treatment for diabetes, vascular disease, lung disease, and is used in chemotherapy for the treatment of cancer. The manufacturing and cleaving method described in FIG. 4 is the same for all semiconductor material electroacupuncture needles.

In another embodiment of the invention, the semiconductor electroacupuncture needle 602 is partly insulated. The insulation material 604 can be, for example, 4228 Red Insulating Varnish, which is known in the chemical art and is available, for example, from MG Chemicals, Burlington, Ontario, Canada. 4228 Red Insulating Varnish can be applied as a very thin coating, 6 micron to 8 micron. The insulating coating provides resistance to the brittleness of the needles. Other insulating materials can also be used. Portions of the semiconductor electroacupuncture needle are left uninsulated to help ensure the flow of electrons comes from the uninsulated portions of the needle. When an insulated semiconductor electroacupuncture needle is in use, current flows from: (1) the exposed tip 606, which in the preferred embodiment is approximately 0.34 cm in length, and from (2) the uninsulated portion near the top of the needle which is also about 0.34 cm in length in the preferred embodiment. There is no current flow from the surface of insulated semiconductor material electroacupuncture needle where insulation material 604 is present. Measurements indicate that the current flow from the two exposed portions is approximately 0.019725 coulombs from each portion when using a lithium-ion 9-volt direct current (VDC) battery providing approximately 1200 milliampere hours (mAh). The insulation material 604 conforms to semiconductor material 404 with few surface imperfections allowing for almost pain free insertion into human/non-human tissue and increases the tensile and sheer strength of the semiconductor electroacupuncture needle.

In yet another embodiment, a light emitting diode is incorporated into the body of the insulated semiconductor material needle 806 with electrical plug hole 802 in the electrode 104. This electrical plug hole 802 provides an insertion point into electrode 104 that permits a strong mechanical and electrical connection to be made with the semiconductor material 404 for light emitting diode insulated semiconductor material needle 806. In at least one embodiment, the light emitting diode is indium phosphide with x and 1-x values to provide either green or red-light emission depending on preference. The Indium Phosphide material can be added using MOCVD epitaxy on a gallium nitride substrate. Using photolithography, photoresist, and etching process to incorporate the Indium Phosphide, one can create a Light Emitting Diode (LED) portion of the semiconductor material electroacupuncture needle.

When the approximate threshold of 10 milliamps (10 mA) at 3.5 Volts D.C. is reached between two or more needles then the light emitting diode insulated semiconductor material needles 806 is activated and emits. When two or more light emitting diode insulated semiconductor material needles 806 are inserted into human/non-human tissue, current and voltage flow is indicated by the emission of light in the visible spectrum from all light emitting diodes associated with insulated semiconductor material electroacupuncture needles. Emission of light from the light emitting diode provides visible indication of current flow between one or more semiconductor material electroacupuncture needles. Light emitting diode function can be incorporated into all types and variations of semiconductor material electroacupuncture needles. At least two semiconductor material electroacupuncture needles must be inserted and at least one of these needles inserted into human/non-human tissue must be a light emitting diode insulated semiconductor material needle 806. Insulation 604 prevents the flow of current from the needle body of light emitting diode insulated semiconductor material needle 806. The current flow between two or more light emitting diode insulated semiconductor material needles 806 is 470 milliamperes (mA) through 10 cm of human/nonhuman tissue.

In another embodiment, one forms a broad electrode insulated semiconductor electroacupuncture needle 902. This particular embodiment is made for specialized treatment applications requiring the electroacupuncture needle to be left for longer periods of time in the tissue of human/non-human subjects. As in the light-emitting diode embodiment, the electrical plug hole 802 provides an insertion point into electrode 104 providing a strong mechanical electrical connection to the semiconductor material 404. In this embodiment, the broad electrode insulated semiconductor electroacupuncture needle 902 allows the insertion into human/non-human tissue up to the bottom of electrode 104. In the preferred version of this embodiment, the broad electrode insulated semiconductor electroacupuncture needs is created to enable an insertion depth from 12.7 mm to 19 mm. This provides broad electrode insulated semiconductor electroacupuncture needle 902 a more secure insertion preventing the needle form falling out of the human/non-human tissue while connected to a control box.

Figure 15:
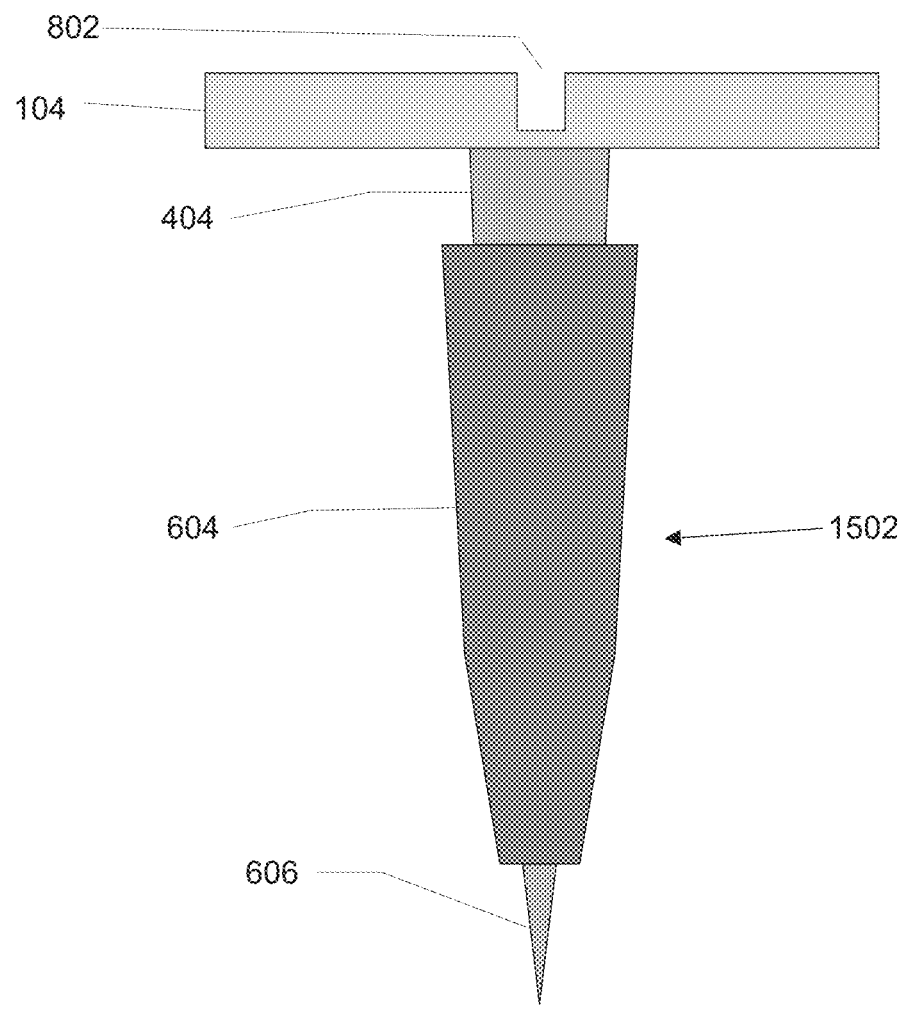
FIG. 15 is a front view of combat insulated semiconductor material electroacupuncture needle.

Combat and military field conditions are notoriously harsh to electronics and other sensitive hardware. Therefore, in another embodiment of the invention one finds a combat insulated semiconductor material electroacupuncture needle 1502 (FIG. 15). In the preferred embodiment the combat insulated semiconductor material electroacupuncture needle 1502 has a length 1504 of 12.7 mm long, a diameter of 0.35 mm at the tip and 3.175 mm at the top under the larger electrode 104. Combat insulated semiconductor material electroacupuncture needle 1502 is designed to be forcefully inserted into human/non-human tissue 1208 to a depth 12.7 mm limited by electrode 104 to permit its use in the treatment of severe trauma such as an amputated limb, gunshot wounds, stab wounds, broken bones, and other serious injuries. In the preferred embodiment, the semiconductor material 404 is 0.34 cm in length, providing a subcutaneous path for current flow of approximately 0.3332 coulombs when the power source is a 40-volt D.C, 5 amp battery. Insulation 604 prevents current flow along the body of combat insulated semiconductor material electroacupuncture needle 1502 and concentrates the emanation of current from the semiconductor material conductive tip 606.

Figure 16:
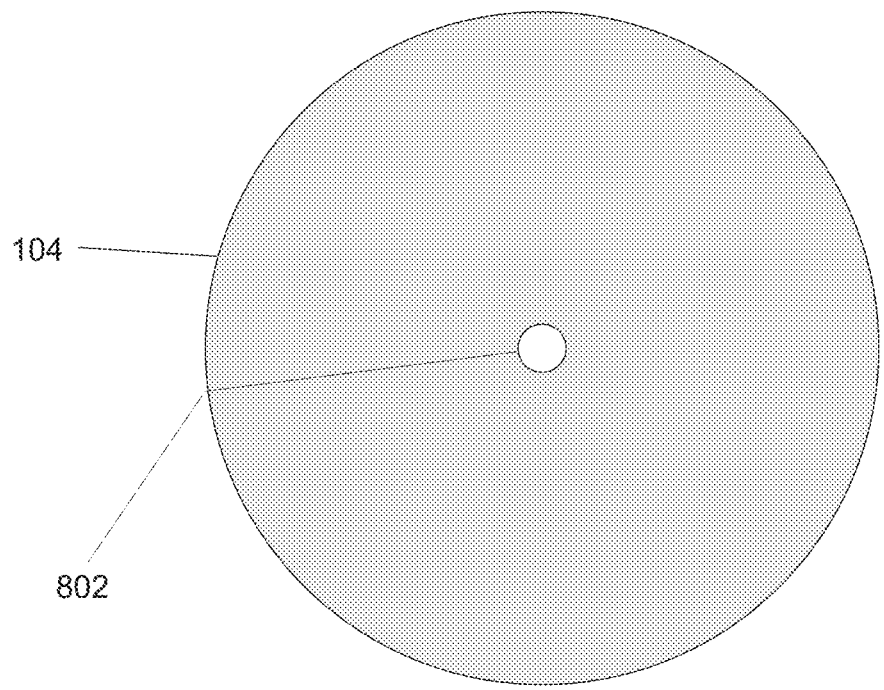
FIG. 16 is a top view showing the electrode of the combat insulated semiconductor material electroacupuncture needle of FIG. 15.

FIG. 16 provides a top view of the electrode 104 for combat insulated semiconductor material electroacupuncture needle 1502. Electrode plug 802 is depicted in the center of the circular electrode 104. Electrode 104 may be other shapes and thicknesses to meet specific requirements.

Figure 19:
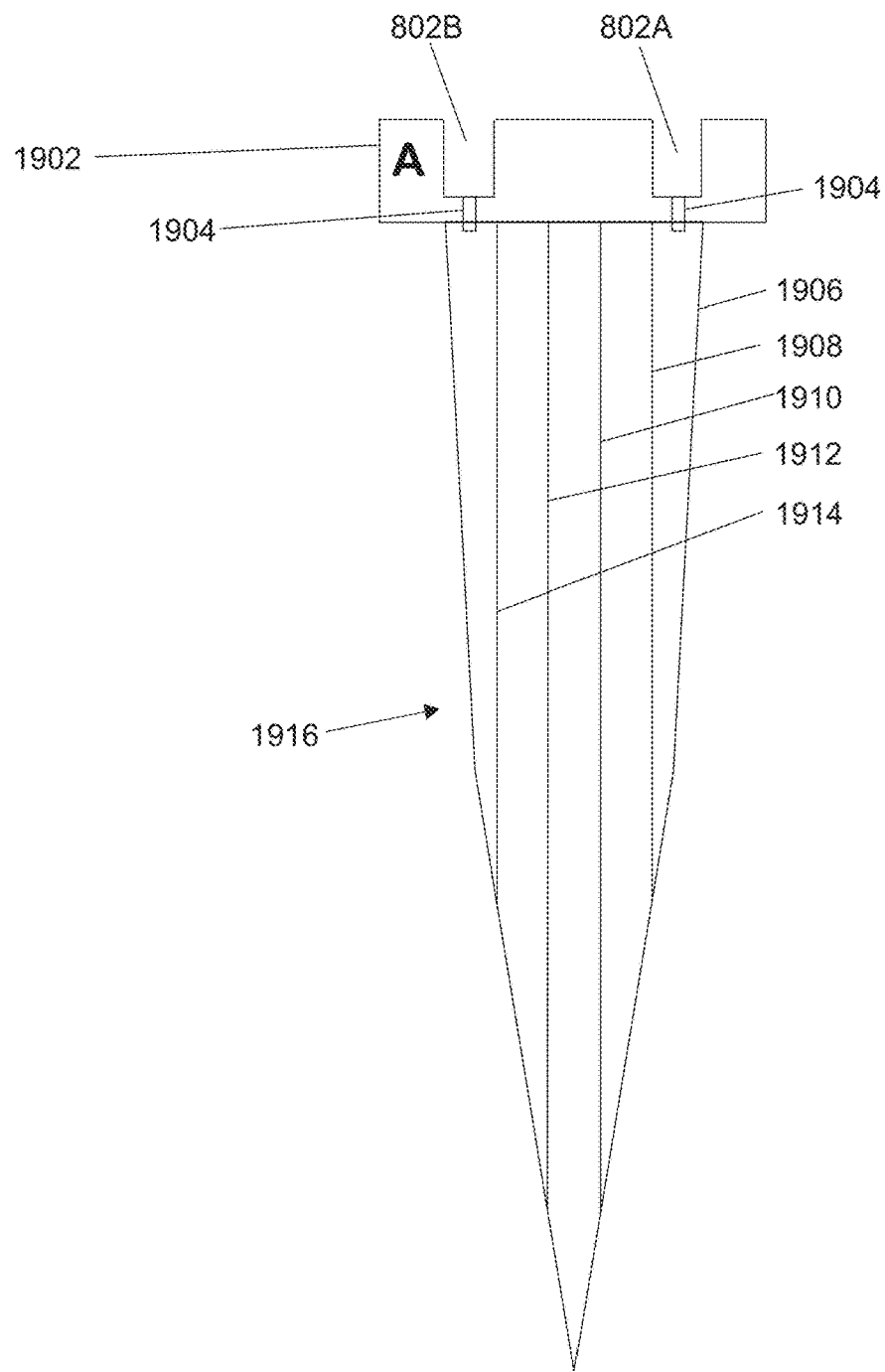
FIG. 19 shows a single needle semiconductor electroacupuncture needle having a non-conducting top with two electrical plugs for the insertion of electrical power, current, waveform, and frequency adjustments into two separate portions of single needle semiconductor electroacupuncture needle.
Figure 20:
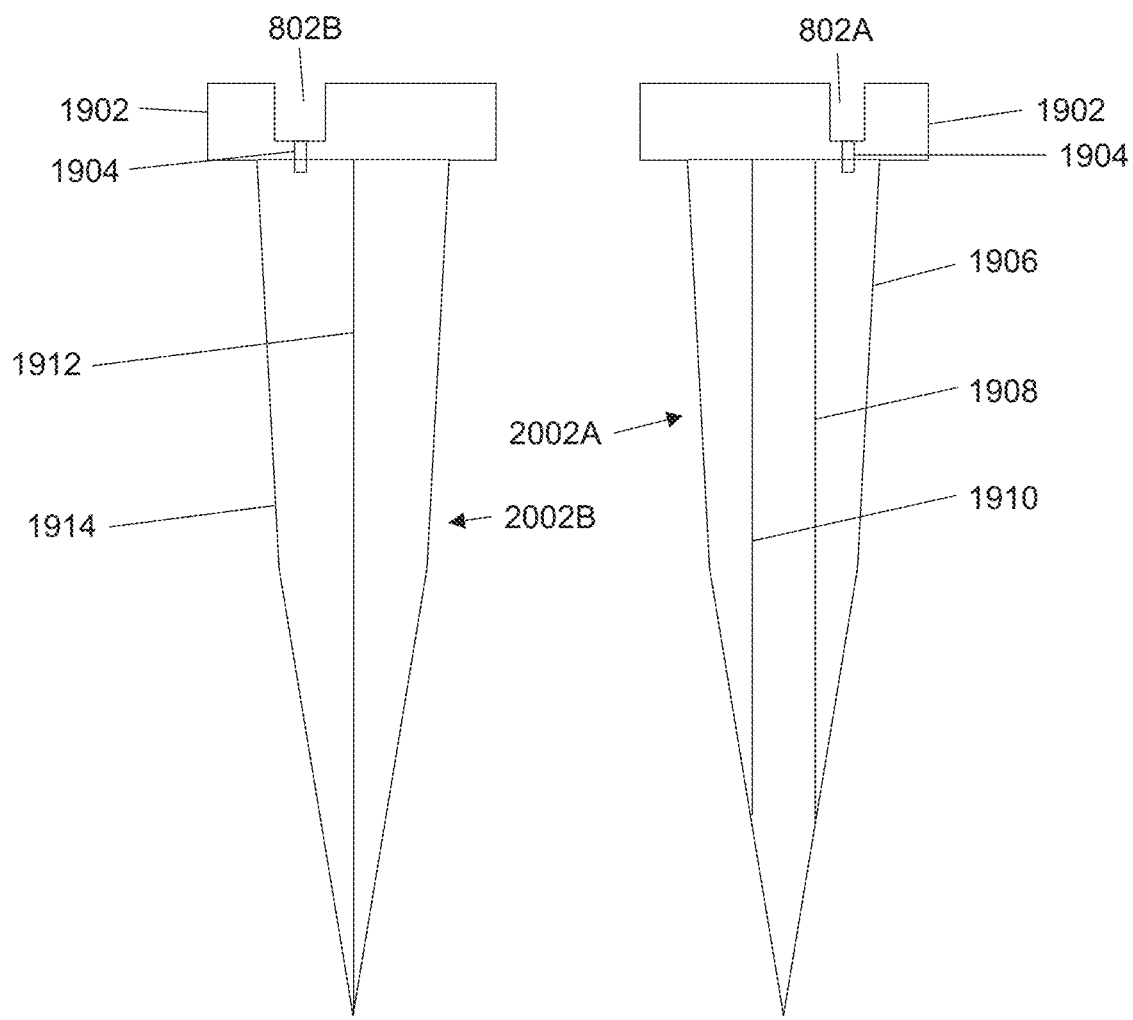
FIG. 20 shows a split semiconductor electroacupuncture needle inserted in close proximity to the two sections with the human/non-human tissue acting as a layer in the overall semiconductor needle device.

FIG. 19 shows another embodiment of the semiconductor electroacupuncture needle is found in the single needle semiconductor electroacupuncture needle 1916 that has a non-conducting top 1902 with two electrical plugs 802A and 802B for the insertion of electrical power, current, waveform, and frequency adjustments into two separate portions of the single needle semiconductor electroacupuncture needle 1916 through its electrical contact 1904. Single needle semiconductor electroacupuncture needle 1916 is used with control box 1016 (FIG. 10) or modified control box 1718 (FIG. 17). electrical plug 802A is connected to the selected control box by negative wire 1204 to one of the negative output plug 1004. Electrical plug 802B is connected to the selected control box by positive wire 1202. Negative electrical input is applied to the semiconductor substrate material 1906 through electrical contact 1904. Current flows through semiconductor material barium 1908, titanium 1910, arsenic 1912, and oxygen 1914. The positive input plug 802B is connected through electrical contact 1904 to the oxygen layer 1914 allowing current flow from the substrate 1906 to the oxygen layer 1914 creating a surface emitting semiconductor device. In the preferred version of this embodiment, the active layer is designated by the bold letter 'A' etched into the non-conducting top 1902. The active layer A faces the traumatic injury. The single needle semiconductor electroacupuncture needle 1916 generates significant current flow into the human/non-human tissue 1208 from the surface of the needle labeled as active 'A' along the entire length of single needle semiconductor electroacupuncture needle 1916.

The single needle semiconductor electroacupuncture needle 1916 can be used for specialized applications requiring greater current flow along the length of single needle semiconductor electroacupuncture needle 1916 such as certain types of cancers, very localized drug addiction treatments, or other applications by varying the content and type of semiconductor materials of the single needle semiconductor electroacupuncture needle 1916.

Finally, there is another embodiment of the invention that is found in the split semiconductor electroacupuncture needle 2002A and 2002B. In typical use, the split semiconductor electroacupuncture needle 2002A and 2002B is inserted into human/non-human tissue with the human/non-human in between the needle points 2002A and 2002B acting as another layer in an overall semiconductor needle device. In the preferred method of use, the human/non-human tissue between 2002A and 2002B contains the area to be treated. Split semiconductor electroacupuncture needle 2002A has a non-conducting top 1902 with electrical plug 802A for the insertion of electrical power, current, waveform, and frequency adjustments into the negative input of split semiconductor electroacupuncture needle 2002A through electrical contact 1904. electrical plug 802A is connected to the selected control box by negative wire 1204 to one of the negative output plug 1004. Negative electrical input is applied to the semiconductor substrate material 1906 through electrical contact 1904. Current flows through the substrate material 1906 into semiconductor material barium 1908, titanium 1910 and into the human/non-human tissue. The positive input plug 802B is connected through electrical contact 1904 to the oxygen layer 1914. Positive electrical wire 1202 connects to positive input plug 802B and to the positive output plug 1006. Split semiconductor electroacupuncture needle 2002A current flows from the substrate material 1906 through the barium semiconductor material layer 1908 and into the titanium semiconductor material layer 1910. Current then flows into the human/non-human tissue and into the arsenic layer 1912, and then into the oxygen semiconductor layer which is connected to the positive input plug 802B. The human/non-human tissue acts as a semiconductor layer in that it conducts current. The human/non-human tissue between split semiconductor electroacupuncture needle 2002B and split semiconductor electroacupuncture needle 2002A is the area to be treated for pain, discomfort relief, or certain medical conditions. The semiconductor material arsenic, or other toxic material, may be added in very small quantities to affect certain types of medical conditions and can be changed to meet specific treatment requirements. Semiconductor materials selected, except for arsenic, are non-toxic and other semiconductor materials can be used instead of the ones suggested. The current flow between the split semiconductor electroacupuncture needles will be approximately 0.017 coulombs.

Figure 10:
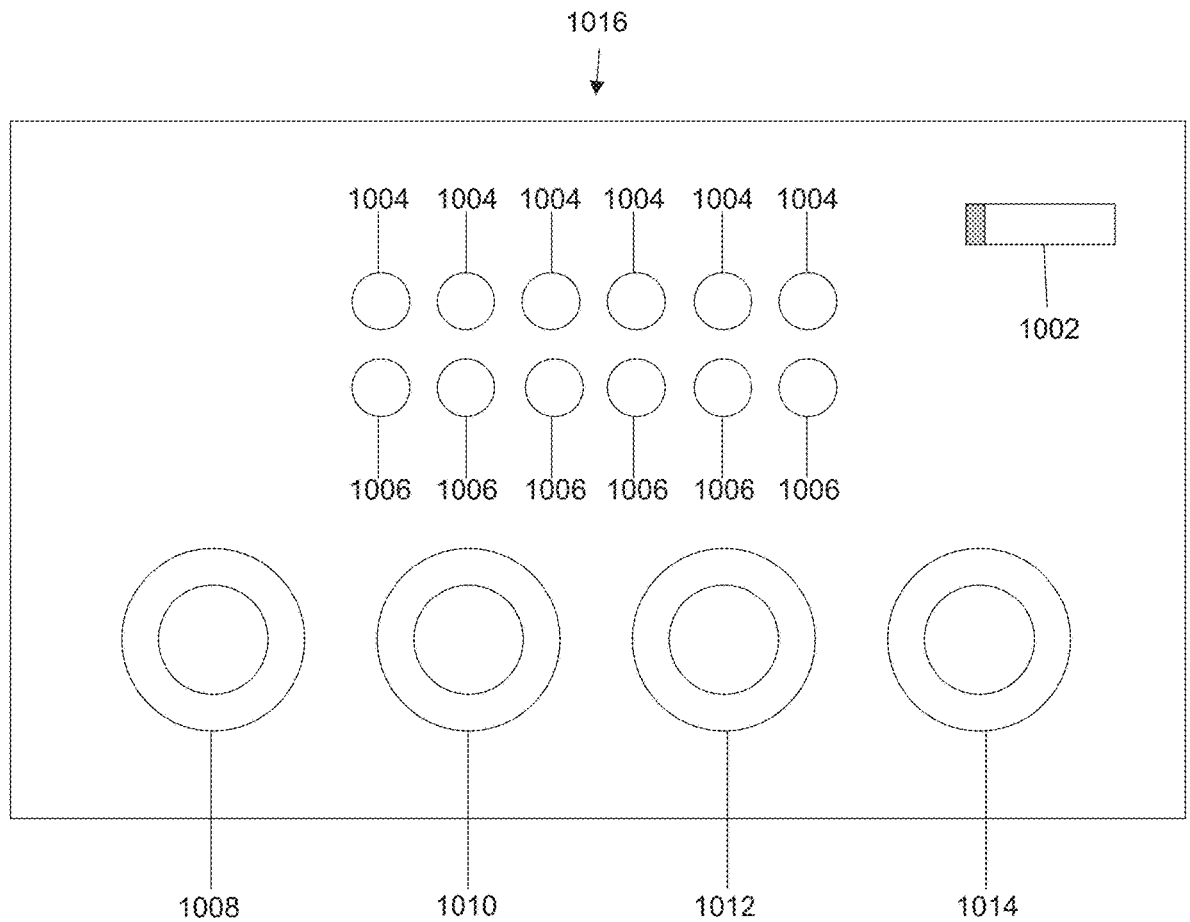
FIG. 10 shows a control box for the application of electrical power in volts, current adjustment in amps, waveform selection, and frequency adjustment to the semiconductor material electroacupuncture needles.

FIG. 10 control box 1016 for the application of, current adjustment in amps 1008, electrical power in volts 1010, waveform selection 1012, and frequency adjustment 104 to the various types of semiconductor material electroacupuncture needles. The outputs for negative connection 1004 and positive connection 1006 also support the signals for waveform and frequency. Control box 1016 has a power switch 1002 from the battery 1018 or another power source. Usually the battery is a Lithium-Ion 9-volt D.C. 1200 milliampere hour (mAh) type. Switch 1002 may be a slide type switch, push type, or any other type of switch to facilitate applying power. Control box 1016 is depicted with 6 pairs of plug-type wire connectors supporting 6 pairs of semiconductor material electroacupuncture needles. More output connectors or fewer output connectors can be used to meet specific applications.

Figure 11:
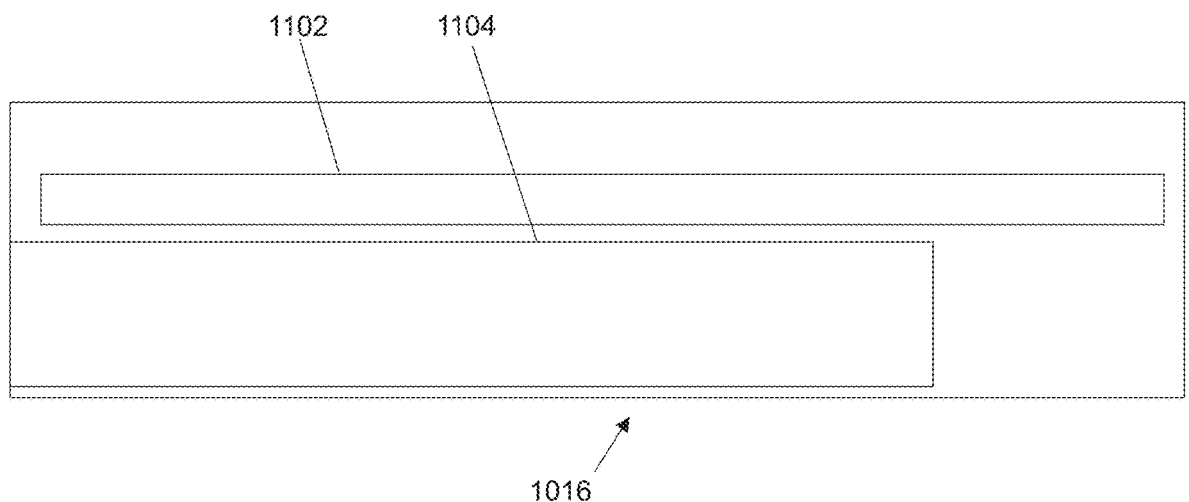
FIG. 11 is a side, internal view of the control box of FIG. 10 depicting the relationship between the printed circuit board (PCB) providing control functions and the battery.

FIG. 11 side, internal view of control box 1016 showing the printed circuit board (PCB) 1020 providing control functions. The printed circuit board 1020 can be modified to provide programmable functions designed for specific medical conditions and treatments. Battery 1018 is selected for what function the control box is expected to perform, and the length of time power is required for a single treatment. The control box can specify, for example, voltage, current, frequency, and waveform. Power can also be supplied to the control from a 120 VAC or 220 VAC electrical outlet.

Figure 12:
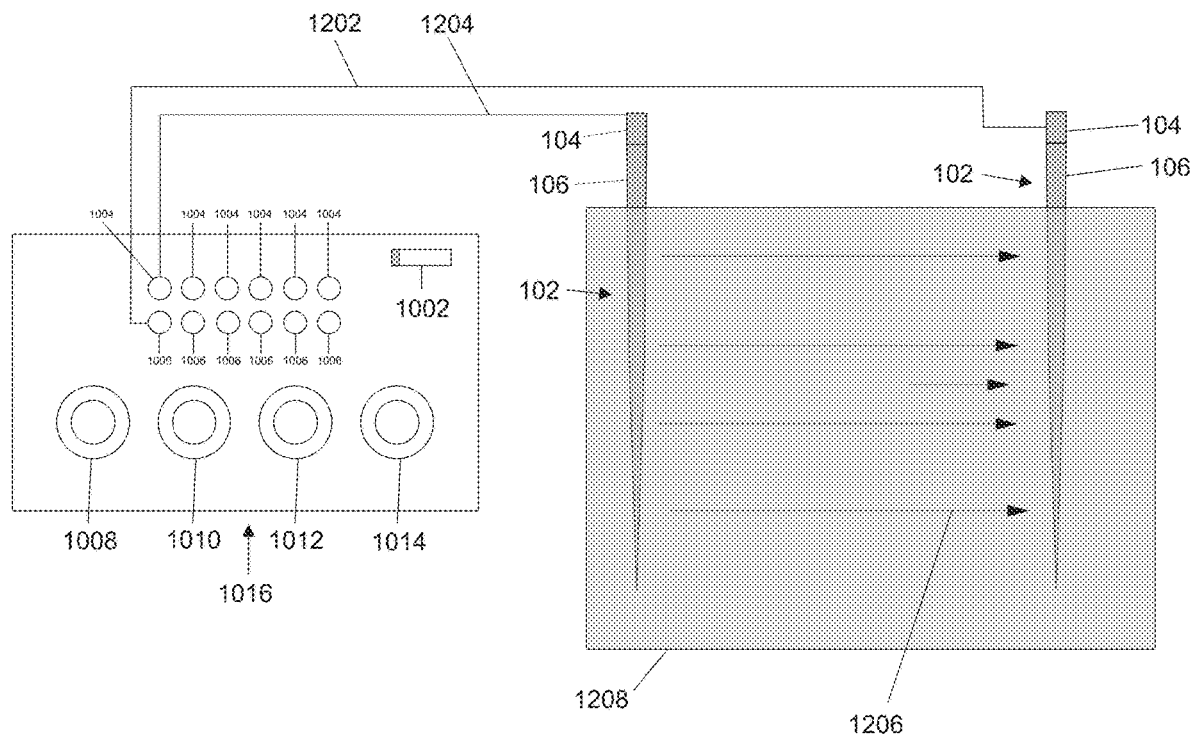
FIG. 12 shows the control box of FIG. 10 attached to current electroacupuncture needles inserted into human/non-human tissue.

FIG. 12 control box 1016 depicted attached to current electroacupuncture needles 102 inserted into human/non-human tissue 1208. Negative control box output 1004 is connected to the negative designated current electroacupuncture needle by wire 1202 and connected to electrode 104 of current electroacupuncture needle 102 using an alligator clip or other mechanical connection method. Positive control box output 1006 is connected to the positive designated current electroacupuncture needle by wire 1204 and connected to electrode 104 of current electroacupuncture needle 102. Current flow 1206 is along the entire length of the current electroacupuncture needle 102. Current controlled by knob 1008, voltage controlled by knob 1010, waveform controlled by knob 1012, and signal frequency controlled by knob 1014 are varied to treat specific medical conditions. Switch 1002 is used to apply or remove power from the current electroacupuncture needles 102. Current flow 1206, is defined as coulombs and propagated between the negative current electroacupuncture needle 102 with a length of 6.35 centimeters and the positive current electroacupuncture needle 102 with a length of 6.35 centimeters through human/non-human tissue 1208. The current flow in coulombs 1206 between the stainless steel electroacupuncture needles with lengths of 6.35 centimeters, a diameter of 0.23 millimeters, a minimum of 11% Chromium. Stainless steel electroacupuncture needles are typically made from Type 304 Stainless Steel, also known as 18/8 and 18/10 for its composition of 18% chromium and 8%/10% nickel, respectively. resulting in a minimum coulomb reduction of approximately 30%, a calculated stainless steel needle resistivity of 0.000205248 ohms at a voltage of 9 Volts D.C. results in a maximum current of 1200 milliamps producing a maximum of 0.027989 Coulombs controlled by knob 1008. The arrows between the electroacupuncture needle indicate coulomb intensity. 1010 is increased in intensity or decreased in intensity relative to what the desired effect is on neurons and the synaptic gap. Waveform 1012 is selected for a desired specific condition treatment. A sawtooth waveform. A sawtooth waveform could be selected to provide a ramped increase in voltage and current followed by a return to a lower level of voltage and current. Frequency of the signal controlled by knob 1014 is used to create effects in combination with current, voltage, and waveform to affect the increased production of L-DOPA and Dopamine which can be used for the treatment of schizophrenia and drug addiction. Endorphin release is stimulated by pain and stress. As pain or stress increase endorphins are released which stimulates the release of dopamine to reduce the perceived level of pan. Combinations of current, voltage, waveform, and frequency applied to current electroacupuncture needles can result in the release of endorphins and the subsequent release of dopamine, this mechanism of the nervous system can possibly be used to treat opioid and other drug addiction.

Figure 13:
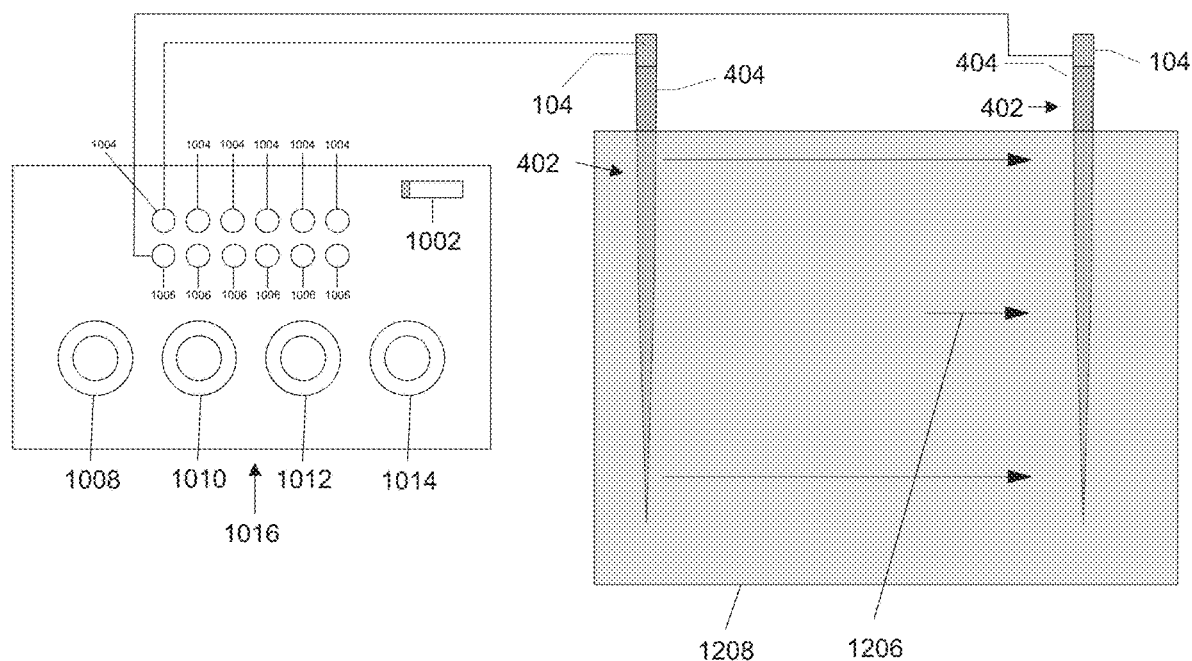
FIG. 13 shows the control box of FIG. 10 attached to semiconductor material electroacupuncture needles inserted into human/non-human tissue.

FIG. 13 control box 1016 depicted attached to semiconductor material electroacupuncture needle 402 inserted into human/non-human tissue 1208. Negative control box output 1004 is connected to the negative designated current electroacupuncture needle by wire 1202 and connected to electrode 104 of semiconductor material electroacupuncture needle 402 using an alligator clip or other mechanical connection method. Positive control box output 1006 is connected to the positive designated current electroacupuncture needle by wire 1204 and connected to electrode 104 of semiconductor material electroacupuncture needle 402. Current flow is along the entire length of the semiconductor material electroacupuncture needle 402. Current controlled by knob 1008, voltage controlled by knob 1010, waveform controlled by knob 1012, and signal frequency controlled by knob 1014 are varied to treat specific medical conditions. Switch 1002 is used to apply or remove power from the semiconductor material electroacupuncture needle 402. Current flow 1206 is generated between the negative semiconductor material electroacupuncture needle 402 and the positive semiconductor material electroacupuncture needle 402 through human/non-human tissue 1208. The current flow in coulombs 1206 between the semiconductor material electroacupuncture needles with lengths of 6.35 centimeters, a diameter of 0.23 millimeters, a calculated semiconductor material electroacupuncture needle resistivity of approximately 50 ohms at a voltage of 9 Volts D.C. results in a maximum current of 180 milliamps producing a maximum of 0.014994 coulombs controlled by knob 1008. The arrows between the electroacupuncture needle indicate coulomb intensity. Voltage 1010 is increased in intensity or decreased in intensity relative to what the desired effect is on neurons and the synaptic gap. Waveform 1012 is selected for a desired specific condition treatment. A sawtooth waveform. A sawtooth waveform could be selected to provide a ramped increase in voltage and current followed by a return to a lower level of voltage and current. Frequency of the signal controlled by knob 1014 is used to create effects in combination with current, voltage, and waveform to affect the increased production of L-DOPA and Dopamine which can be used for the treatment of schizophrenia and drug addiction. Endorphin release is stimulated by pain and stress. As pain or stress increase endorphins are released which stimulates the release of dopamine to reduce the perceived level of pan. Combinations of current, voltage, waveform, and frequency applied to current electroacupuncture needles can result in the release of endorphins and the subsequent release of dopamine, this mechanism of the nervous system can possibly be used to treat opioid and other drug addiction.

Figure 14:
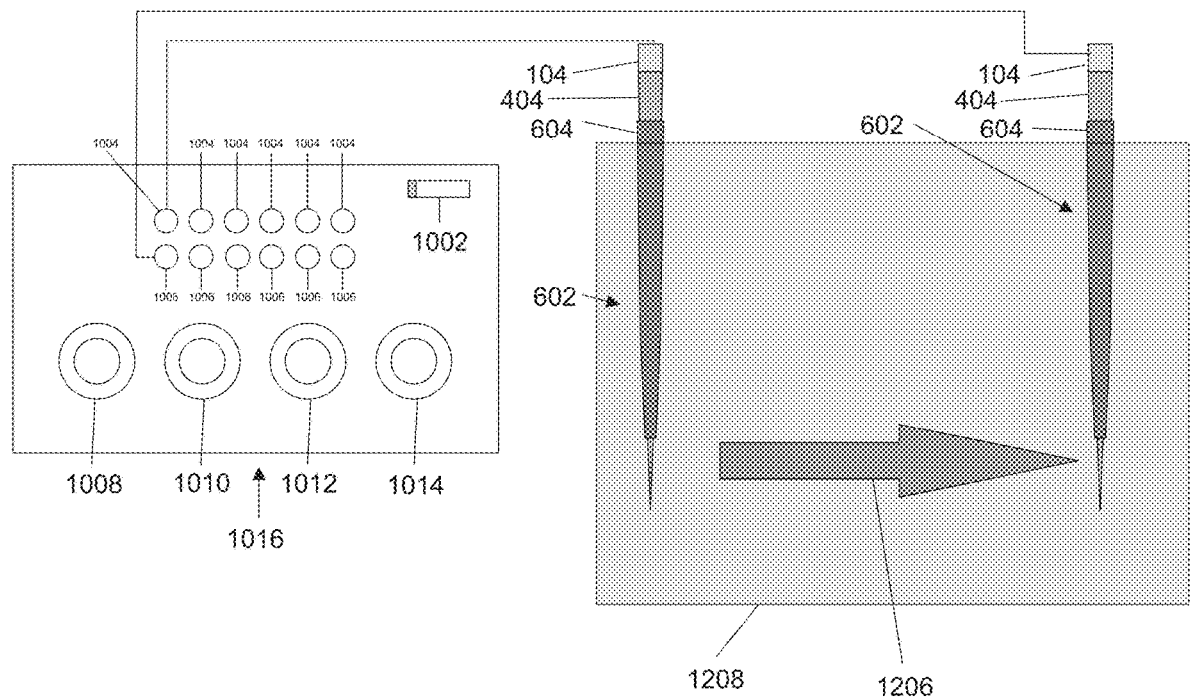
FIG. 14 shows the control box of FIG. 10 attached to insulated semiconductor material electroacupuncture needles inserted into human/non-human tissue.

FIG. 14 control box 1016 depicted attached to insulated semiconductor material electroacupuncture needle 602 inserted into human/non-human tissue 1208. Negative control box output 1004 is connected to the negative designated insulated semiconductor material electroacupuncture needle 602 by wire 1202 and connected to electrode 104 of insulated semiconductor material electroacupuncture needle 602 using an alligator clip or other mechanical connection method. Positive control box output 1006 is connected to the positive designated insulated semiconductor material electroacupuncture needle 602 by wire 1204 and connected to electrode 104 of insulated semiconductor material electroacupuncture needle 602. Current flow 1206 is from the semiconductor material conductive tip 606. Current controlled by knob 1008, voltage controlled by knob 1010, waveform controlled by knob 1012, and signal frequency controlled by knob 1014 are varied to treat specific medical conditions. Switch 1002 is used to apply or remove power from insulated semiconductor material electroacupuncture needle 602. Current flow 1206 is generated between the negative insulated semiconductor material electroacupuncture needle 602 and the positive insulated semiconductor material electroacupuncture needle 602 through human/non-human tissue 1208. The current flow in coulombs 1206 between the insulated semiconductor material electroacupuncture needles with lengths of 6.35 centimeters, a diameter of 0.23 millimeters, two spaces of insulated material at the top and bottom of 0.34 cm, a calculated semiconductor material electroacupuncture needle resistivity of approximately 50 ohms at a voltage of 9 Volts D.C. results in a maximum current of 180 milliamps producing a maximum of 0.078915754 coulombs. The top uninsulated 0.34 cm section of the insulated semiconductor material electroacupuncture needle does not conduct through air. Coulombs are controlled by knob 1008. The intensity of current flow 1206 is suggested by the larger arrow. Voltage 1010 is increased in intensity or decreased in intensity relative to what the desired effect is on neurons and the synaptic gap. Waveform 1012 is selected for a desired specific condition treatment. A sawtooth waveform. A sawtooth waveform could be selected to provide a ramped increase in voltage and current followed by a return to a lower level of voltage and current. Frequency of the signal controlled by knob 1014 is used to create effects in combination with current, voltage, and waveform to affect the increased production of L-DOPA and Dopamine which can be used for the treatment of schizophrenia and drug addiction. Endorphin release is stimulated by pain and stress. As pain or stress increase endorphins are released which stimulates the release of dopamine to reduce the perceived level of pan. Combinations of current, voltage, waveform, and frequency applied to current electroacupuncture needles can result in the release of endorphins and the subsequent release of dopamine, this mechanism of the nervous system can possibly be used to treat opioid and other drug addiction.

Figure 17:
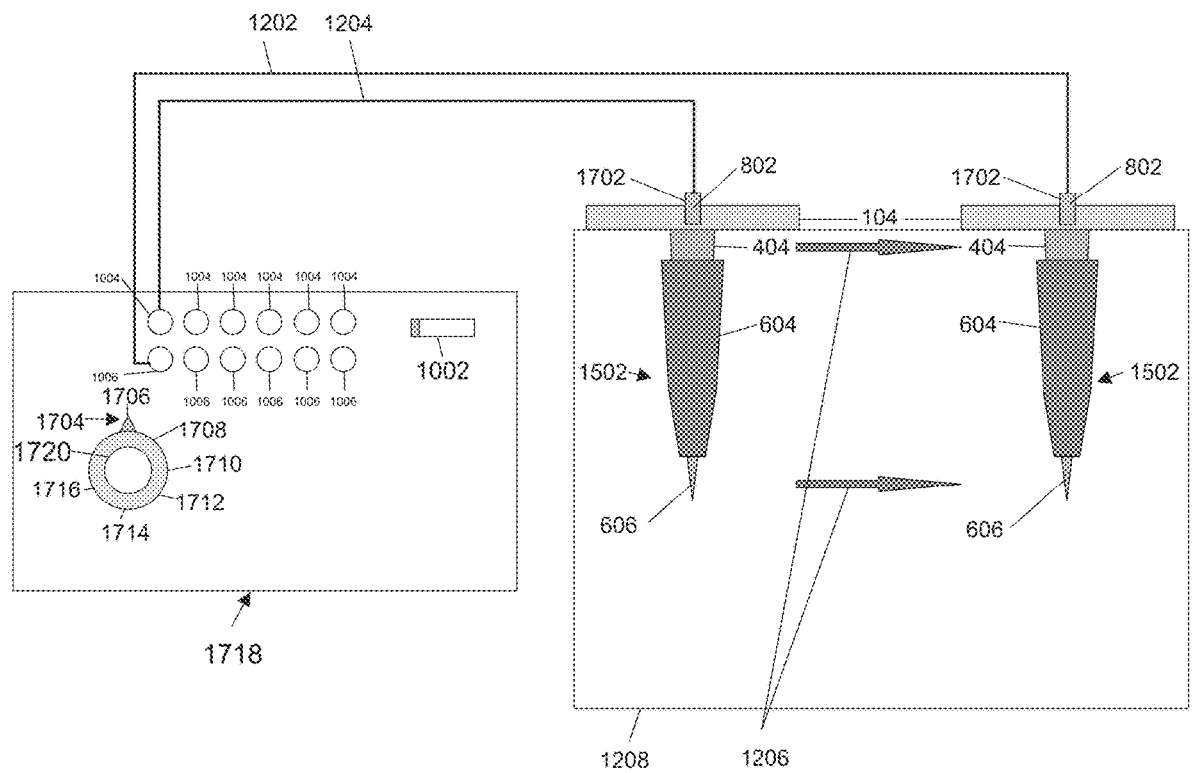
FIG. 17 show a control box modified for a combat insulated semiconductor material electroacupuncture needle connected to a pair of combat insulated semiconductor material electroacupuncture needles inserted into human/non-human tissue.

FIG. 17 Illustrates the relationship between the modified control box 1718 and the inserted into human/non-human tissue 1208 combat insulated semiconductor material electroacupuncture needles 1502. Switch 1002 is depicted as a slide type switch but may be a more rugged type of switch to meet specific environmental conditions such as a water tight push on type switch for applying power to the combat insulated semiconductor material electroacupuncture needles 1502 through one of the negative or positive output plugs 1004 or 1006. The combat insulated semiconductor material electroacupuncture needle 1502 is designated as positive or negative and connected to the appropriate output plug for negative 1004 or positive 1006. One of the negative output plugs 1004 is connected to negative wire 1204 which is attached to negative electrode plug 1702 and inserted into the electrode plug hole 802 in electrode 104 which provides signals and power to negative designated combat insulated semiconductor material electroacupuncture needle 1502. One of the positive output plugs 1006 is connected to positive wire 1202 which is attached to positive electrode plug 1702 and inserted into the electrode plug hole 802 in electrode 104 which provides signals and power to positive designated combat insulated semiconductor material electroacupuncture needle 1502. Signal and power are selected by control knob 1720. Position indicator pointer 1704 provides positive indication of function selected. Position 1706 is he "OFF" position. The functions are shown as Amputation 1708. Amputation 1708 position is used for pain relief following the removal of arms, legs, hands, feet, or other significant body parts. Amputation 1708 position is preset for the appropriate voltage, current, frequency, and waveform for the specific traumatic injury. Gutshot 1710 position is used for gunshot wounds to the abdominal cavity. Gutshot 1710 position is preset for the appropriate voltage, current, frequency, and waveform for the specific traumatic injury. Gunshot 1712 is the position selected for gunshot wounds to any part of the human/non-human body. Gunshot 1712 position is preset for the appropriate voltage, current, frequency, and waveform for the specific traumatic injury. Broken Bones position 1714 is used for any broken bones ranging from phalanges to large bones such as the femur, pelvis, or spinal injuries. Broken Bones position 1714 position is preset for the appropriate voltage, current, frequency, and waveform for the specific traumatic injury. Laceration position 1716 is used to relieve discomfort from deep lacerations in human/non-human tissue 1208. Laceration 1716 position is preset for the appropriate voltage, current, frequency, and waveform for the specific traumatic injury. The battery used modified control box 1718 is significantly more powerful, more in the range of supplying up to 40 volts D.C. at 5.0 Amps or more. Current flow at the subcutaneous depth from exposed semiconductor material 404 from the negative designated combat insulated semiconductor material electroacupuncture needle 1502 to the positive designated combat insulated semiconductor material electroacupuncture needle 1502 provide pain and discomfort relief at or below the surface of the human/non-human tissue 1208. Insulation 604 prevents current flow along the body of combat insulated semiconductor material electroacupuncture needle 1502 and concentrates current flow from the semiconductor material conductive tip 606 providing pain and discomfort relief at a deeper level. The strength of the current flow 1206 is indicated by the size of the directional arrow.

Figure 18:
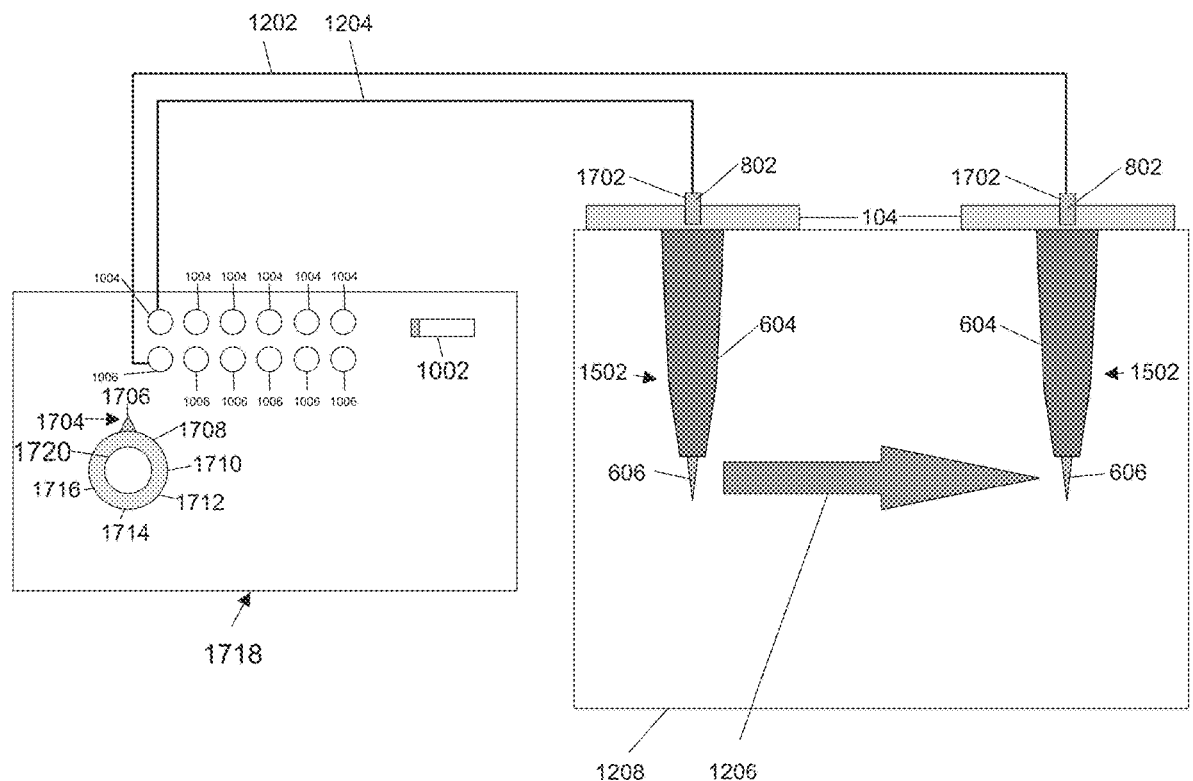
FIG. 18 shows the modified control box of FIG. 17 connected to a pair of combat insulated semiconductor material electroacupuncture needles inserted into human/non-human tissue, with the insulation material extended to cover the exposed semiconductor material in the combat insulated semiconductor material electroacupuncture needle.

FIG. 18 The insulation material 604 is extended to cover the exposed semiconductor material 404 in the combat insulated semiconductor material electroacupuncture needle. The 0.35 cm of exposed semiconductor material tip 606 provides 0.4165 coulombs. FIG. 18 illustrates the relationship between the modified control box 1718 and the inserted into human/non-human tissue 1208 combat insulated semiconductor material electroacupuncture needles 1502. Switch 1002 is depicted as a slide type switch but may be a more rugged type of switch to meet specific environmental conditions such as a water tight push on type switch for applying power to the combat insulated semiconductor material electroacupuncture needles 1502 through one of the negative or positive output plugs 1004 or 1006. The combat insulated semiconductor material electroacupuncture needle 1502 is designated as positive or negative and connected to the appropriate output plug for negative 1004 or positive 1006. One of the negative output plugs 1004 is connected to negative wire 1204 which is attached to negative electrode plug 1702 and inserted into the electrode plug hole 802 in electrode 104 which provides signals and power to negative designated combat insulated semiconductor material electroacupuncture needle 1502. One of the positive output plugs 1006 is connected to positive wire 1202 which is attached to positive electrode plug 1702 and inserted into the electrode plug hole 802 in electrode 104 which provides signals and power to positive designated combat insulated semiconductor material electroacupuncture needle 1502. Signal and power are selected by control knob 1720. Position indicator pointer 1704 provides positive indication of function selected. Position 1706 is he "OFF" position. The functions are shown as Amputation 1708 position is used for pain relief following the removal of arms, legs, hands, feet, or other significant body parts. Gutshot 1710 position is used for gunshot wounds to the abdominal cavity. Gutshot 1710 position is preset for the appropriate voltage, current, frequency, and waveform for the specific traumatic injury. Gunshot 1712 is the position selected for gunshot wounds to any part of the human/non-human body. Gunshot 1712 position is preset for the appropriate voltage, current, frequency, and waveform for the specific traumatic injury. Broken Bones position 1714 is used for any broken bones ranging from phalanges to large bones such as the femur, pelvis, or spinal injuries. Broken Bones position 1714 position is preset for the appropriate voltage, current, frequency, and waveform for the specific traumatic injury. Laceration position 1716 is used to relieve discomfort from deep lacerations in human/non-human tissue 1208. Laceration 1716 position is preset for the appropriate voltage, current, frequency, and waveform for the specific traumatic injury. The battery used modified control box 1718 is significantly more powerful, more in the range of supplying up to 40 volts D.C. at 5.0 Amps or more. Insulation 604 prevents current flow along the body of combat insulated semiconductor material electroacupuncture needle 1502 and concentrates current flow from the semiconductor material conductive tip 606 providing pain and discomfort relief at a deeper level. The strength of the current flow 1206 is indicated by the size of the directional arrow.

Implementation of Methods

Semiconductor products are made through a variety of methods. The method used to create the semiconductor electroacupuncture needles described herein involves, in the preferred method, epitaxy. One first starts with sintering $BaTiO_3$ powder to get a ceramic block of piezoelectric material. There are a number of semiconductor precursors for barium and titanium permitting the use of metalorganic vapor-phase epitaxy (MOVPE), also known as organometallic vapor-phase epitaxy (OMVPE) or metalorganic chemical vapor deposition (MOCVD) using an aerosol-assisted liquid delivery system. The MOCVD method is described in the paper. Schafer, Patrick, Ritter, Sigrun, Ganster, Ralf, Ehrhart, Peter, Hoffmann, Susanne, and Waser, Rainer. "*Preparation of $(Pb_xBa1-x)TiO3$ thin films by MOCVD using an aerosol-assisted liquid delivery system*," https://doi.org/10.1080/10584580008222265. Although epitaxy is typically aimed towards the creation of thin films of semiconductor materials, one can modify the process to permit the creation of greater thickness semiconductor materials. Prasad Alluri, Prashant Majhi, Derek Tang & Sandwip K. Dey (1998) *ECR-MOCVD of the Ba-Sr-Ti-O system below 400° C. Part I: Processing, Integrated Ferroelectrics*, 21:1-4, 305-318, DOI: 10.1080/10584589808202072. Several substrate materials are available for epitaxy there are primarily, silicon, gallium nitride, sapphire, silicon carbide, and emerald. Care should be used in the introduction of oxygen as small amounts of oxygens result in large changes in the electrical characteristics. In other implementations, one may add strontium as a non-toxic material which provides for enhanced current flow. The temperature is frequently varied during epitaxy to reduce crystal lattice mismatch.

Once one has a block of $BaTiO_3$ one can proceed to etching and dividing it using a laser system to provide the individual semiconductor electroacupuncture needles with a diameter of 0.35 millimeters. In some embodiment, between 500 and 900 individual needles can be produced. Using a 300 mm wafer of gallium nitride (GaN) and the tertiary compound $BaTiO_3$ via the use of aerosol assisted liquid delivery system metalorganic chemical vapor deposition (MOCVD) at or below 400° C., approximately 1,500 semiconductor material electroacupuncture needles of lengths varying from 12.7 mm to 127 mm can be manufactured depending on the initial substrate (wafer) diameter. The needles are cut the from the 300 mm wafer using laser etching to the desired needle width.

Figure 6:
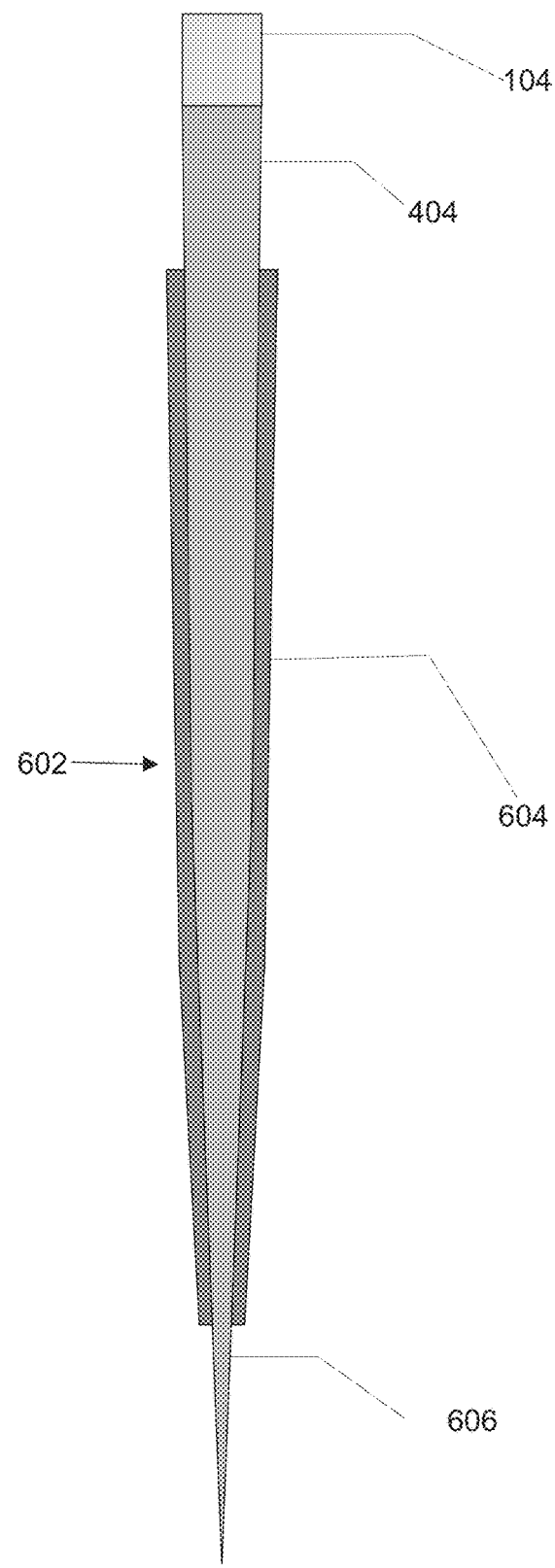
FIG. 6 is a cutaway view of an insulated semiconductor material electroacupuncture needle, showing the relationship between the insulating material and the semiconductor material.
Figure 7:
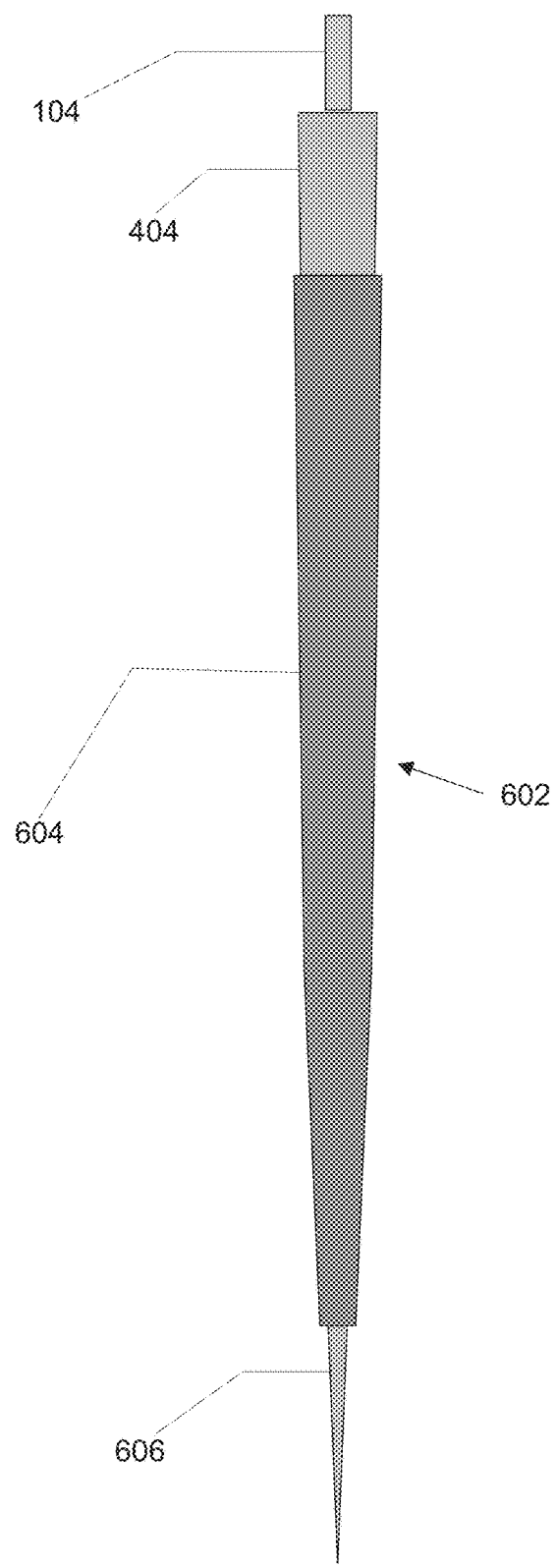
FIG. 7 is a side view of an insulated semiconductor material electroacupuncture needle showing the semiconductor material conductive tip, the fully coated insulating material, and the electrode.
Figure 8:
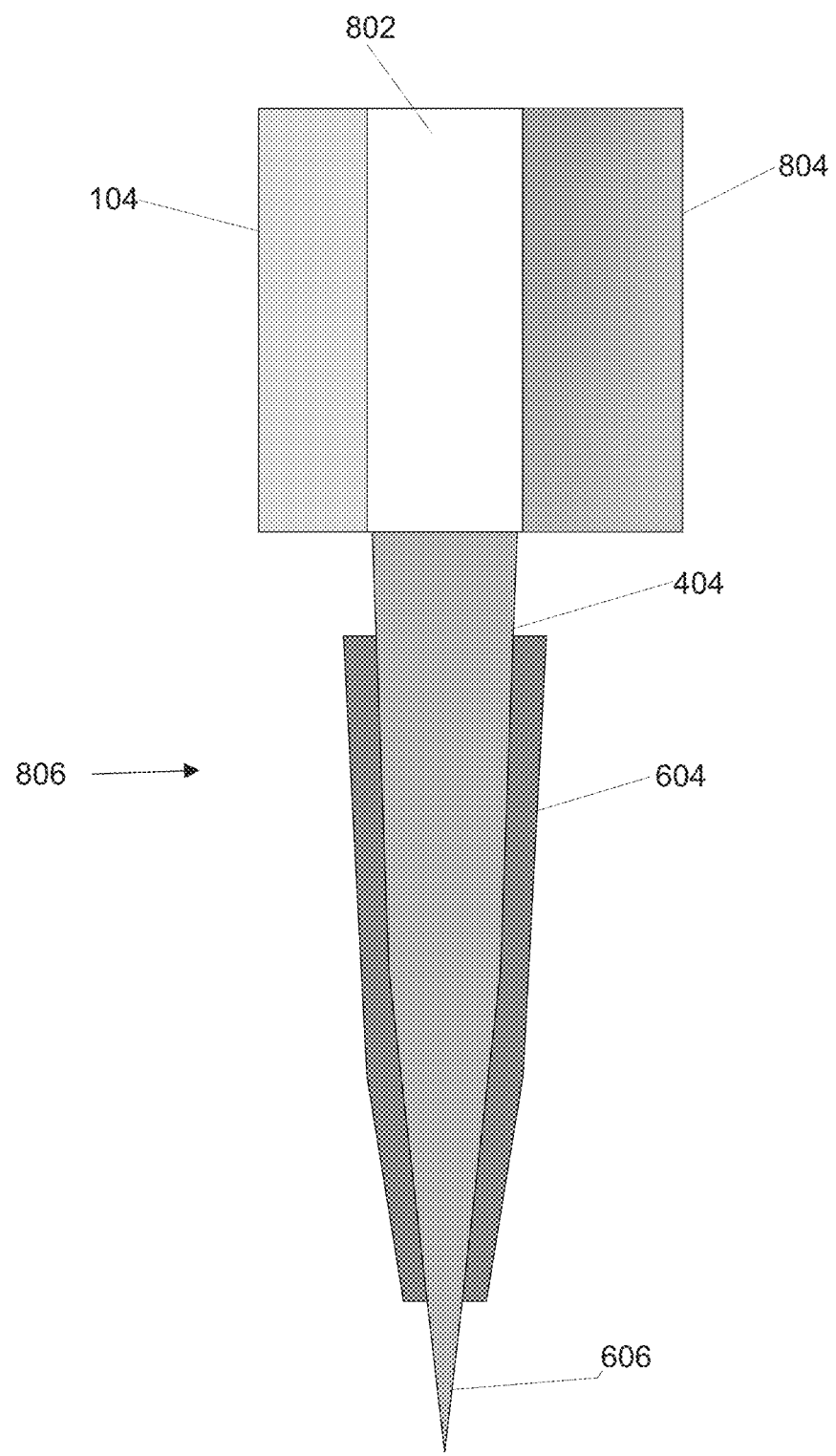
FIG. 8 is a front cutaway view of light emitting diode insulated semiconductor material needle with an added electrical plug hole in the electrode.
Figure 9:
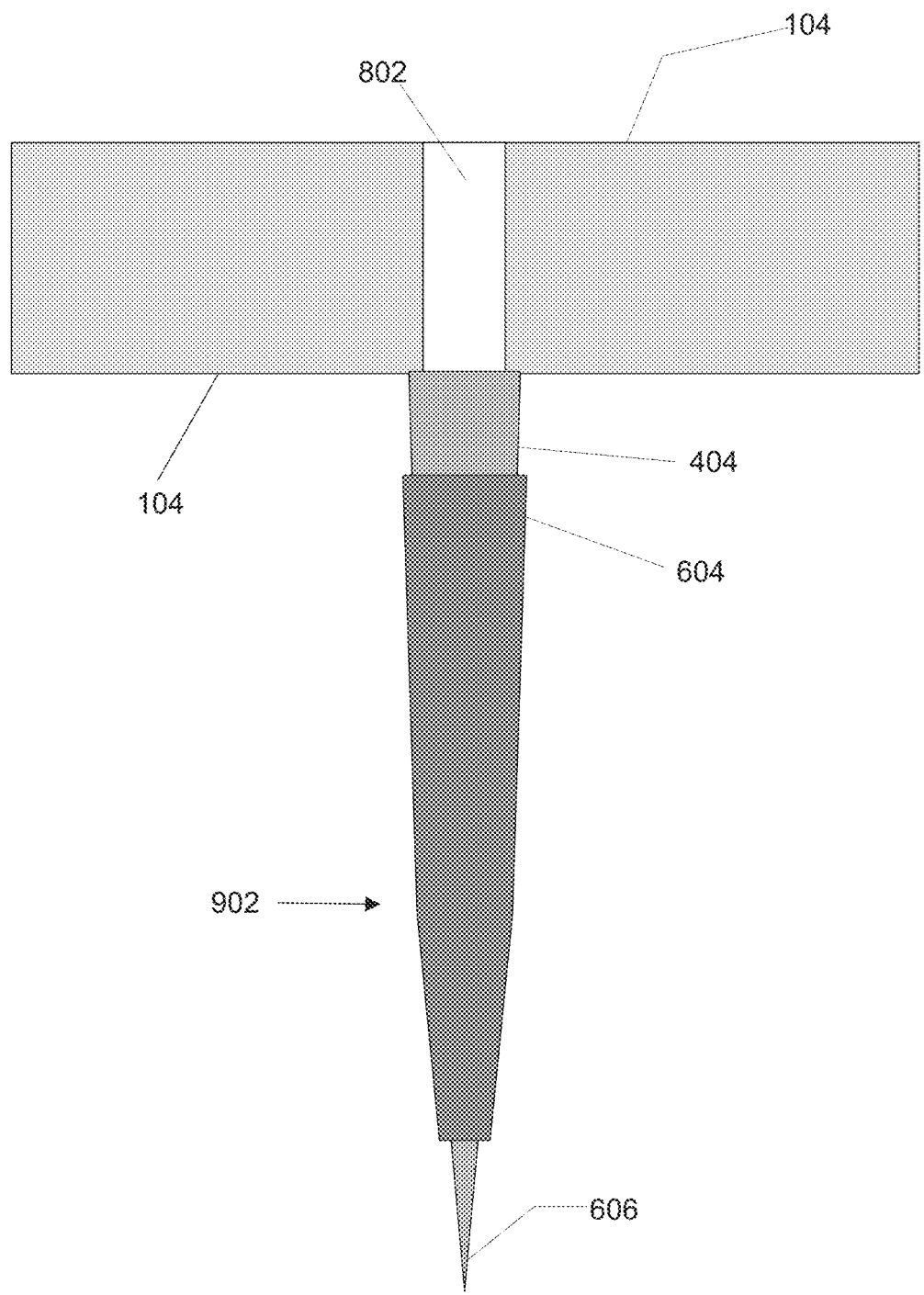
FIG. 9 shows a broad electrode insulated semiconductor electroacupuncture needle for specialized treatment applications requiring the insulated semiconductor material needle be left for longer periods of time in the tissue of human/non-human subjects.

These semiconductor electroacupuncture needles can be insulated to increase their functionality. FIG. 6 shows a cutaway view of insulated semiconductor material electroacupuncture needle 602. The insulation material 604 is, in the preferred embodiment, 4228 Red Insulating Varnish. This varnish is to be applied with a maximum thickness of 38 microns (0.0381 mm) as smooth homogenous coating in order to minimize discomfort when used. The semiconductor material electroacupuncture needles without insulation are completely immersed in the 4228 Red Insulating Varnish or similar material.

Once the varnish has cured it is removed with a laser, ground off, or scraped off exposing the tip. The cured coating presents no known hazard.

Semiconductor material electroacupuncture needles may also be constructed using metal organic chemical vapor deposition (MOCVD), Metalorganic vapor-phase epitaxy (MOVPE), and molecular beam epitaxy (MBE) using commercially available volatile precursors to produce the desired deposits on the substrate. A typical example for a semiconductor electroacupuncture needle could involve the use of gallium nitride or gallium Phosphide as a substrate, a graded buffer layer to reduce crystal lattice structure mismatch, a layer of N-type (negative doped) Indium 0.27 gallium 0.73 phosphide, an undoped layer of indium 0.3 gallium 0.7P, and a P-doped layer (positive doped) indium 0.26 gallium 0.74 phosphide. Compounds with a Binary, discrete lattice constant material such as gallium arsenide, gallium antimonide, indium phosphide, gallium phosphide, indium arsenide, and indium antimonide are also available for manufacturing semiconductor electroacupuncture needles and are readily commercially available. These materials permit using MOCVD, MOVPE, and MBE. The temperature is frequently varied during epitaxy to reduce crystal lattice mismatch. The temperature varies typically between 420-480 Centigrade, for MOCVD temperature vary from 500-1500 Centigrade. For an explanation of the factors involved, please see the following article: https://royalsocietypublishing.org/doi/pdf/10.1098/rsos.171757.

Figure 21:
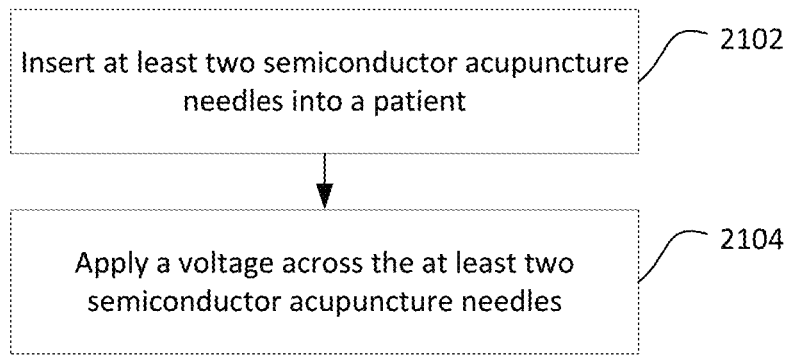
FIG. 21 is a flow chart showing a method of using a semiconductor electro acupuncture needle.

FIG. 21 shows a method of electroacupuncture. In step 2102, at least two semiconductor acupuncture needles are inserted into a patient. In step 2104, a voltage is applied across the two semiconductor acupuncture needles.

Figure 22:
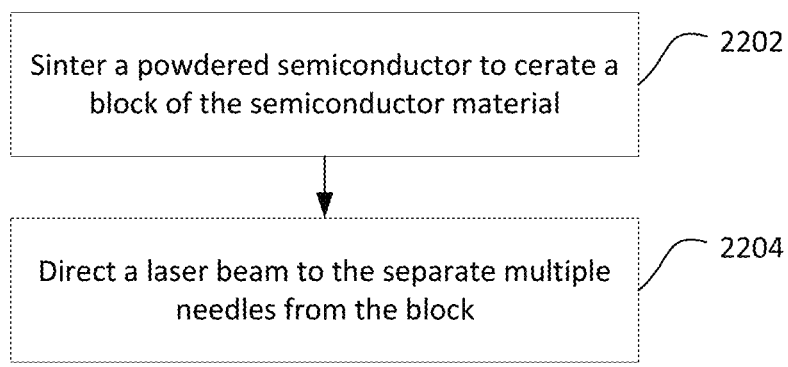
FIG. 22 is a flow chart showing a method of making a semiconductor electro acupuncture needle.

FIG. 22 shows a method for manufacturing electroacupuncture needles from a semiconductor. In step 2202, one scinters powdered semiconductor to create a block of the semiconductor. In step 2204, one directs a laser beam to cut and separate multiple needles from the semiconductor block. in at least one embodiment of the method, the powdered semiconductor used in the scintering comprises BaTiO3. One can also use this method to create electroacupuncture needles from a semiconductor that include a light emitting diode.

Figure 23:
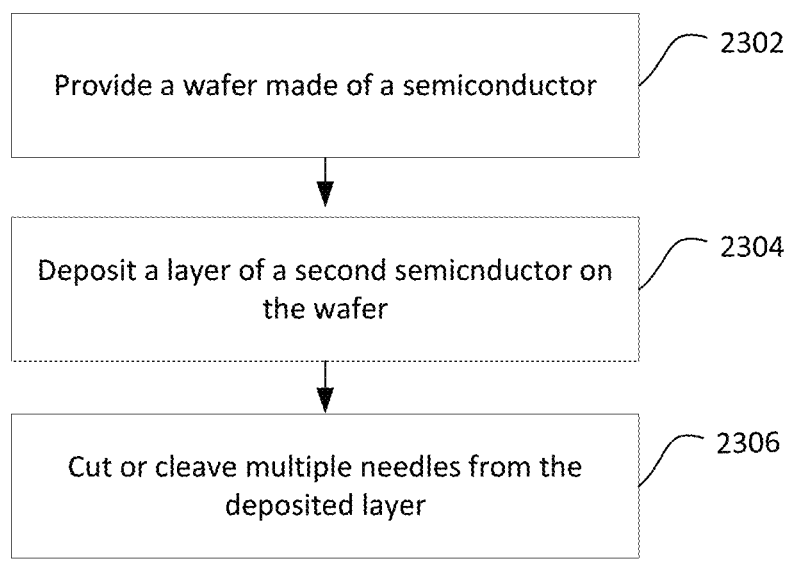
FIG. 23 is a flow chart showing another method of making a semiconductor electro acupuncture needle.

FIG. 23 shows another method for the manufacturing of electroacupuncture needles from a semiconductor. in step 2302, one provides a wafer comprising a semiconductor. in step 2304, one deposits a layer of a second semiconductor onto the wafer of step 2302. In step 2306, one cuts, or cleaves, individual semiconductor electroacupuncture needles from the layer of semiconductor deposited in step 2304. The list of possible semiconductors one can use for the wafer in step 2302 comprises silicon, gallium nitride, sapphire, silicon carbide or emerald. One of the ways to deposit a layer of semiconductor onto the wafer in step 2304 comprises depositing an epitaxial layer using metalorganic vapor phase epitaxy.

While the description above described the use of semiconductor needles for electroacupuncture, semiconductor needles can also be used for conventional acupuncture without running a current through the needles.

CONCLUSION

Historically, electroacupuncture needles have been made with a variety of metallic and/or homogenous materials such as iron, gold, and copper. While needles made from these materials may exhibit higher current flow at lower voltages, current flow in needles made from semiconductor materials will outperform homogenous and metallic materials at sufficiently high voltages. A method for making and using semiconductor electroacupuncture needles has been disclosed. In additional to a basic semiconductor electroacupuncture needle, a number of alternative embodiments have also been disclosed, including those created to target specific treatment issues and applications. Although specific implementations are illustrated and described herein, it will be appreciated by those of ordinary skill in the art that any arrangement which is calculated to achieve the same purpose may be substituted for the specific implementations shown. This application is intended to cover any adaptations or variations.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations.

The invention claimed is:

1. A semiconductor electroacupuncture needle comprising:
   a shaft having a first end and a second end;
   a pointed tip at a first end of the shaft; and
   an electrode contact region at a second end,
   in which the shaft and the tip comprise a semiconductor material and the shaft comprises $BaTiO_3$.

2. The semiconductor electroacupuncture needle of claim 1 in which the shaft further comprises strontium.

3. The semiconductor electroacupuncture needle of claim 1, in which the shaft comprises $BaTiAsO_3$.

4. The semiconductor electroacupuncture needle of claim 1 in which the shaft has a diameter of between 0.25 mm and 0.45 mm.

5. The semiconductor electroacupuncture needle of claim 1, further comprising an insulating layer covering a portion of the shaft to restrict the flow of current from the portion of the shaft.

6. The semiconductor electroacupuncture needle of claim 5 in which the portion of the shaft covered by the insulating layer begins between 0.35 and 0.45 cm from the tip.

7. The semiconductor electroacupuncture needle of claim 1 in which a portion of the of the semiconductor electroacupuncture needle comprises a biologically active material.

8. The semiconductor electroacupuncture needle of claim 1 in which the biologically active material comprises a toxic material.

9. The semiconductor electroacupuncture needle of claim 1 further comprising a light-emitting diode supported by the electroacupuncture needle and electrically connected when current is flowing from the needle into a patient.

10. The semiconductor electroacupuncture needle of claim 9 wherein the light-emitting diode comprises indium phosphide.

11. The semiconductor electroacupuncture needle of claim 9 wherein the light-emitting diode lights above a threshold current of 10 mA.

12. The semiconductor electroacupuncture needle of claim 1, wherein the electrode has two opposing, flat sides adapted for the use of affixing an electrical connector.

13. The semiconductor electroacupuncture needle of claim 1 wherein the diameter of the shaft at the top is greater than 5 times the diameter of the shaft at the tip.

14. A method of manufacturing an electroacupuncture needle in accordance with claim 1, the method comprising:
   providing a wafer of a first semiconductor;
   depositing on the wafer a layer of a second semiconductor; and
   cutting from the deposited layer multiple needles.

15. The method of claim 14 in which the wafer comprises a material selected from the group consisting of silicon, gallium nitride, sapphire, silicon carbide or emerald.

16. The method of claim 14 in which depositing on the wafer the layer of semiconductor material comprising depositing an epitaxial layer using metalorganic vapor phase epitaxy.

17. The method of claim 14 further comprising cleaving the wafer to produce needles.

18. A method of manufacturing an electroacupuncture needle in accordance with claim 1, the method comprising:
   sintering a powdered semiconductor to create a block of the semiconductor material; and
   directing a laser beam toward the block to separate multiple needles from the block, in which the powdered semiconductor comprises BaTiO3.

19. A semiconductor electroacupuncture needle, comprising:
   a shaft having a first end and a second end;
   a pointed tip at a first end of the shaft; and
   an electrode contact region at a second end,
   in which the shaft and the tip comprise a semiconductor material, a portion of the semiconductor electroacupuncture needle comprises a biologically active material, the biologically active material comprises a toxic material, and the toxic material comprises arsenic.

20. A method of electroacupuncture, comprising:
   inserting at least two semiconductor acupuncture needles into a patient; and
   applying a voltage across the two semiconductor acupuncture needles, at least one of the at least two semiconductor needles comprise $BaTiO_3$.

21. The method of claim 20 in which applying a voltage across the two semiconductor acupuncture needle comprises applying a voltage to produce a current of between 0.20 mA and 180 mA).

22. The method of claim 20 in which inserting at least two semiconductor acupuncture needles into a patient comprises inserting at least one semiconductor needle that has an insulting coating over a portion of the semiconductor needle.

23. The method of claim 22 in which:
   inserting at least one semiconductor needle that has an insulating coating over a portion of the semiconductor needle comprises inserting at least one semiconductor needle that has an insulting coating over a portion of the semiconductor needle adapted to be positioned at the surface of the patient's skin; and applying a voltage across the two semiconductor acupuncture needles produces an electrical current primarily below the patient's skin.

24. The method of claim 20 in which inserting at least two semiconductor acupuncture needles into a patient comprises inserting at least one semiconductor acupuncture needles having a tip diameter of 0.45 mm or less and having a shaft diameter at a position away from the tip of between 1 mm and 5 mm into a patient.

25. The method of claim 24 in which applying a voltage across the two semiconductor acupuncture needles comprises applying a voltage to product a current of 180 mA.

26. A method of manufacturing an electroacupuncture needle, the method comprising:
  sintering a powdered semiconductor to create a block of the semiconductor material; and
  directing a laser beam toward the block to separate multiple needles from the block, in which the powdered semiconductor comprises $BaTiO_3$.

* * * * *